United States Patent [19]
Goldstein et al.

[11] Patent Number: 5,599,808
[45] Date of Patent: Feb. 4, 1997

[54] AQUEOUS INDOLOCARBAZOLE SOLUTIONS

[75] Inventors: Joel D. Goldstein, King of Prussia, Pa.; Joseph L. Herman, Wilmington, Del.

[73] Assignee: Cephalon, Inc., West Chester, Pa.

[21] Appl. No.: 383,414

[22] Filed: Feb. 3, 1995

Related U.S. Application Data

[63] Continuation-in-part of Ser. No. 199,390, Feb. 18, 1994, abandoned.

[51] Int. Cl.⁶ .......................... A61K 31/55; A61K 47/10; A61K 47/12; A61K 47/00
[52] U.S. Cl. ........................ 514/211; 514/57; 514/59; 514/724; 514/772.3; 514/781; 514/784
[58] Field of Search ................ 514/211, 57, 59, 514/772.3, 781, 784, 724

[56] References Cited

U.S. PATENT DOCUMENTS

| | | | |
|---|---|---|---|
| 4,877,776 | 10/1989 | Murakata et al. | 514/43 |
| 4,923,986 | 5/1990 | Murakata et al. | 540/545 |
| 5,043,335 | 8/1991 | Kleinschroth et al. | 514/211 |
| 5,093,330 | 3/1992 | Caravatti et al. | 514/211 |

FOREIGN PATENT DOCUMENTS

| | | |
|---|---|---|
| 0508792A1 | 10/1992 | European Pat. Off. . |
| 0575955A1 | 12/1993 | European Pat. Off. . |
| 60-257652 | 6/1987 | Japan . |
| 62-120388 | 6/1987 | Japan . |
| 62-155285 | 7/1987 | Japan . |
| 60-295172 | 7/1987 | Japan . |
| 60-295173 | 7/1988 | Japan . |
| 63-295589 | 12/1988 | Japan . |
| 62-327858 | 12/1988 | Japan . |
| 63-295588 | 12/1988 | Japan . |
| 62-327859 | 12/1988 | Japan . |
| 5-247056 | 9/1993 | Japan . |
| WO88/07045 | 9/1988 | WIPO . |
| WO92/17181 | 10/1992 | WIPO . |
| WO92/18507 | 10/1992 | WIPO . |
| WO93/00909 | 1/1993 | WIPO . |
| WO93/08809 | 5/1993 | WIPO . |
| WO94/02488 | 2/1994 | WIPO . |

OTHER PUBLICATIONS

Berg et al. "K–252a Inhibits Nerve Growth Factor–induced trk Proto–oncogene Tyrosine Phosphorylation and Kinase Activity" J. Biol. Chem. 267:13–16 (1992).

Gribble et al., "Synthetic Approaches to Indolo[2,3-a]carbazole Alkaloids. Syntheses of Arcyriaflavin A and AT2433–B Aglycone," Tetrahedron 48:8869–8880, 1992.

Kase et al. "K–252 Compounds, Novel and Potent Inhibitors of Protein Kinase C & Cyclic Nucleotide–Dependent Protein Kinases" Biochem. and Biophys. Res. Comm. 142:436–440 (1987).

Moody et al. "Synthesis of the Staurosporine Aglycon" J. Org. Chem. 57:2105–2114 (1992).

Nakanishi et al. "K–252b, c and d, Potent Inhibitors of Protein Kinase C From Microbial Origin" J. Antibiot. 39:1066–1071 (1986).

Steglich et al. "Indole Pigments from the Fruiting Bodies of the Slime Mold *Arcyria denudata*" Angew. Chem. Ind. Ed. Engl. 19:459–460 (1980).

Yasuzawa et al. "The Structures of the Novel Protein Kinase C Inhibitors K–252a, b, c and d" J. Antibiot. 39:1072–1078 (1986).

*Primary Examiner*—Kevin E. Weddington
*Attorney, Agent, or Firm*—Fish & Richardson P.C.

[57] ABSTRACT

Disclosed herein are aqueous indolocarbazole solutions. In one embodiment, the invention features a solution comprising: (1) an indolocarbazole; (ii) a selected organic solvent being present in a concentration of between about 1% and about 99% by weight inclusive, (iii) a dispersant being present in a concentration of between about 0.25% and about 10% by weight inclusive; (iv) water being present in a concentration of between 0% and about 99% by weight inclusive, and (v) a polyethylene glycol being present in a concentration of between 0% and about 60% by weight inclusive.

24 Claims, 7 Drawing Sheets

5,599,808

AQUEOUS INDOLOCARBAZOLE SOLUTIONS

This application is a continuation-in-part of 08/199,390, filed Feb. 8, 1994, now abandoned.

BACKGROUND OF THE INVENTION

This invention concerns aqueous solutions of indolocarbazoles suitable for pharmaceutical use.

Indolocarbazoles exhibit useful antifungal, antimicrobial and antitumor properties. Some indolocarbazoles such as K-252a modulate neurotrophin responses by affecting protein kinase activity (Berg et al. *J. Biol. Chem.* 267:13–16 (1992)). Indolocarbazoles can be isolated from a wide variety of microorganisms including *S. staurosporeus, N. aerocoligenes, Actinomadura* and *Nocardiopsis* sp using known methods (Kase et al., BBRC 142:436–440, (1987)). The synthetic preparation of several indolocarbazoles has been described (U.S. Pat. Nos. 4,923,986; 4,877,776; 5,093,330, each incorporated by reference herein; Moody et al., *J. Org. Chem.* 57:2105–2114 (1992), WO 93/08809). Several indolocarbazoles have been characterized and include, but are not limited to, staurosporine, rebeccamycin, (Moody et al., supra), K-252a, K-252b (Kase et al., supra), K-252c (also called staurosporine aglycon by Moody et al., supra), K-252d, and derivatives thereof (published Japanese patent applications 60-257652, 60-295172, 62-327858, 62-327859, and 60-295173).

Nakanishi et al. (*J. Antibodies*, 34:1066, (1986)) describe the insolubility of K-252a, K-252b, K-252c, and K-252d in water. U.S. Pat. No. 5,093,330 reports dry pharmaceutical preparations (dragees, tablets and capsules) of staurosporine derivatives that may contain polyethylene glycol and polyvinylpyrrolidone. U.S. Pat. No. 5,043,335 and WO 93/00909 each disclose pharmaceutical compositions including an indolocarbazole.

SUMMARY OF THE INVENTION

Indolocarbazoles such as K-252a, K-252b, K-252c, and K-252d are insoluble in water, but soluble in non-aqueous, toxic solvents. An indolocarbazole dissolved in a non-aqueous toxic solvent, an indolocarbazole solution exhibiting incomplete solubilization (e.g., a colloidal solution) in aqueous solution, or an indolocarbazole in dry form are each not useful for many pharmaceutical and biological applications. It would be useful to have an aqueous and non-toxic solution capable of solubilizing indolocarbazoles for pharmaceutical or biological applications.

In general, the invention features a solution comprising an indolocarbazole; between about 1% and about 99% by weight inclusive ("bwi") of a selected organic solvent; between about 0.25% and 10% bwi of a dispersant; between 0% and about 99% bwi of water; and between 0% and about 99% bwi of polyethylene glycol. Preferably, the concentration of the indolocarbazole is at least about 100 µg/ml.

In another aspect, the solution comprises an indolocarbazole; between about 1% and about 10% bwi of propylene glycol selected organic solvent; between about 1% and about 10% bwi of polyvinylpyrrolidone (dispersant) having a k value of 17; between about 50% and 97% bwi of water; and between about 1% and about 30% bwi of a polyethylene glycol having an average molecular weight of between about 200 and about 400. Most preferably, the concentration of the indolocarbazole is at least about 100 µg/ml.

In another aspect, the solution comprises an indolocarbazole; between about 90% and about 99% bwi of propylene glycol selected organic solvent; and between about 1% and about 10% bwi of polyvinylpyrrolidone (dispersant) having a k value of 17. Most preferably, the concentration of the indolocarbazole is at least about 0.5 mg/ml.

In another aspect, the invention features an aqueous solution including an indolocarbazole, preferably at a concentration of at least 0.5 mg/ml; a polyethylene glycol, preferably any one of a PEG-300, PEG-400, PEG-600, or PEG-1000; and at least one of a polyoxyethylene sorbitan fatty acid ester; benzyl alcohol, preferably at a concentration between 1% and 5% by weight inclusive; a polyethylene glycol 4-isooctylphenyl ether; or a non-cytotoxic detergent. Preferably, the aqueous solution further includes polyvinylpyrrolidone, between 1% and 15% by weight inclusive.

In another aspect, the invention features an aqueous solution comprising at least 0.5 mg/ml of an indolocarbazole; between 30% and 60% by weight inclusive of a polyethylene glycol; and at least one of i) between 1% and 15% by weight inclusive of a polyoxyethylene sorbitan fatty acid ester; ii) between 1% and 5% by weight inclusive of benzyl alcohol; iii) between 5% and 15% by weight inclusive of a polyethylene glycol 4-isooctylphenyl ether; or iv) between 1% and 5% by weight inclusive of a non-cytotoxic detergent.

In another aspect, the invention features an aqueous solution including at least 0.5 mg/ml of an indolocarbazole; between 30% and 60% by weight inclusive of a polyethylene glycol; between 1% and 15% by weight inclusive of a polyvinylpyrrolidone; and at least one of i) between 1% and 15% by weight inclusive of a polyoxyethylene sorbitan fatty acid ester; ii) between 1% and 5% by weight inclusive of benzyl alcohol; iii) between 5% and 15% by weight inclusive of a polyethylene glycol 4-isooctylphenyl ether; or iv) between 1% and 5% by weight inclusive of a non-cytotoxic detergent.

In a related aspect, the invention features an aqueous solution including at least 0.5 mg/ml of an indolocarbazole; between 30% and 60% by weight inclusive of a polyethylene glycol; between 1% and 15% by weight inclusive of a polyvinylpyrrolidone; between 1% and 5% by weight inclusive of a benzyl alcohol; and at least one of between 1% and 15% by weight inclusive of a polyoxyethylene sorbitan fatty acid ester; between 5% and 15% by weight inclusive of a polyethylene glycol 4-isooctylphenyl ether; or between 1% and 5% by weight inclusive of a non-cytotoxic detergent.

An indolocarbazole unit, as used herein, has the general formula shown below:

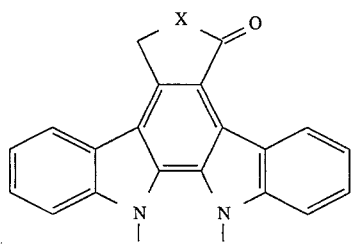

wherein
a) X is either O or N—; and
b) N— represents a nitrogen atom capable of bonding with another atom.

An indolocarbazole, as used herein, is a chemical compound including an indolocarbazole unit. Examples of preferred indolocarbazoles include, but are not limited to, K-252a, K-252b, K-252c, K-252d, staurosporine, and indolocarbazoles described below.

Given the intended objective of the indolocarbazole, i.e., as a therapeutic, it is noted that the solution is most preferably capable of being administered to a mammal, e.g., a human, without toxic consequences. Accordingly, the non-indolocarbazole components of the solution (e.g. the so-called inactive ingredients) are most preferably GRAS ingredients, i.e., Generally Recognized As Safe. GRAS ingredients can be obtained from, e.g., the "Inactive Ingredient Guide" published by the United States Food and Drug Administration (Division of Drug Information Resources), HFD82, Room 8B16, 5600 Fishers Lane, Rockville, Md. 20857 ("Guide"). The Guide provides a listing of all inactive ingredients present in approved drug products or conditionally approved drug products currently marketed for human use.

A "selected organic solvent," as used herein, is a material comprising as its principal component molecules with at least one atom with a pair of unshared electrons, preferably an oxygen or nitrogen atom. Although not wishing to be bound thereby, the inventors postulate that because the indolocarbazoles contain atoms with unshared electrons, selected organic solvents aid in the solubilization thereof. Exemplary selected organic solvents include propylene glycol, polytheylene glycol (PEG), benzyl alcohol, N-N-dimethyl acetamide, ethyl acetate and acetic acid. Most preferably, the selected organic solvent is propylene glycol.

A "dispersant" as used herein, is a material comprising as its principal component a substance which promotes the formation and stabilization of a dispersion of one substance in another, e.g., an indolocarbazole in a solution as disclosed. Exemplary dispersants include polyvinylpyrrolidone, dextran, cellulose, polyoxyethylene sorbitan fatty acid ester, polyethylene glycol 4-isooctylphenyl ether, and non-cytotoxic detergents.

A polyethylene glycol, as used herein, is a liquid or solid polymer of the general formula $H(OCH_2CH_2)_nOH$, where n is greater than or equal to 4.

A polyvinylpyrrolidone (i.e., PVP), as used herein, is a polymer consisting of linear groups of 1-vinyl-2-pyrrolidone with mean molecular weights between 10,000 and 360,000. Examples include polyvinylpyrrolidones with k values between 18 and 32, inclusive (see The United States Pharmacopeia 22, pg. 1118).

A polyoxyethylene sorbitan fatty acid ester, as used herein, is a non-ionic detergent which may consist of a mixture of fatty acids. Commercially available examples include Tween™ 20, Tween™ 80, Tween™ 40, Tween™ 60 and Tween™ 85.

A polyethylene glycol 4-isooctylphenyl ether, as used herein, is a molecule of the general formula $C_8H_{17}$—$C_6H_4$—O—$(C_2H_4$—$O)_n$H, where n=7–10. Examples include Triton™ X-100, Triton™ X-114, Triton™ X-405, Triton™ N-101, Triton™ X-15, Triton™ 770, Triton™ X-405R, and other commercially available Triton™ biological detergents (Sigma Chemical Company Product Listing, pg. 1544, (1992)).

A non-cytotoxic detergent, as used herein, is a non-toxic detergent acceptable for use in cell culture. Commercially available examples include Pluronic™ L61, Pluronic™ L64, and Pluronic™ F68.

Colloid, or colloidal as used herein, is an indolocarbazole aggregate in a finely divided, unsolubilized state that resists sedimentation, diffusion, and filtration.

A lower alkyl, as used herein, is a straight-chain or branched alkyl group having 1 to 6 carbon atoms, inclusive, preferably 1 to 3 carbons such as methyl, ethyl, propyl, isopropyl, butyl, isobutyl, sec-butyl, tert-butyl, pentyl, neopentyl and hexyl. Aryl, as used herein, means an aryl group having 6 to 10 carbon atoms, inclusive, such as phenyl and naphthyl. Heterocyclic, as used herein, are pyrrolyl, pyranyl, thiopyranyl, pyridyl, thiazolyl, imidazolyl, pyrimidyl, triazinyl, indolyl, quinolyl, purinyl, or benzothiazolyl groups. Halogen, as used herein, means fluorine, chlorine, bromine, or iodine. Pro, Ser, Glc, and Gly, as used herein, refer to proline, serine, glucose, or glycine, respectively.

A percent (%), as used herein, is given as a weight percent (w/w).

As used then, the term "about" means +/− 10%. For example, "about 10" means between 9 and 11.

As used then, the term "aqueous" in reference to a solution means the solution comprises at least about 1% water.

Those skilled in the art will appreciate from the following examples that aqueous solutions of the invention are capable of solubilizing indolocarbazoles not explicitly mentioned below.

DESCRIPTION OF THE PREFERRED EMBODIMENTS

Figure 1:
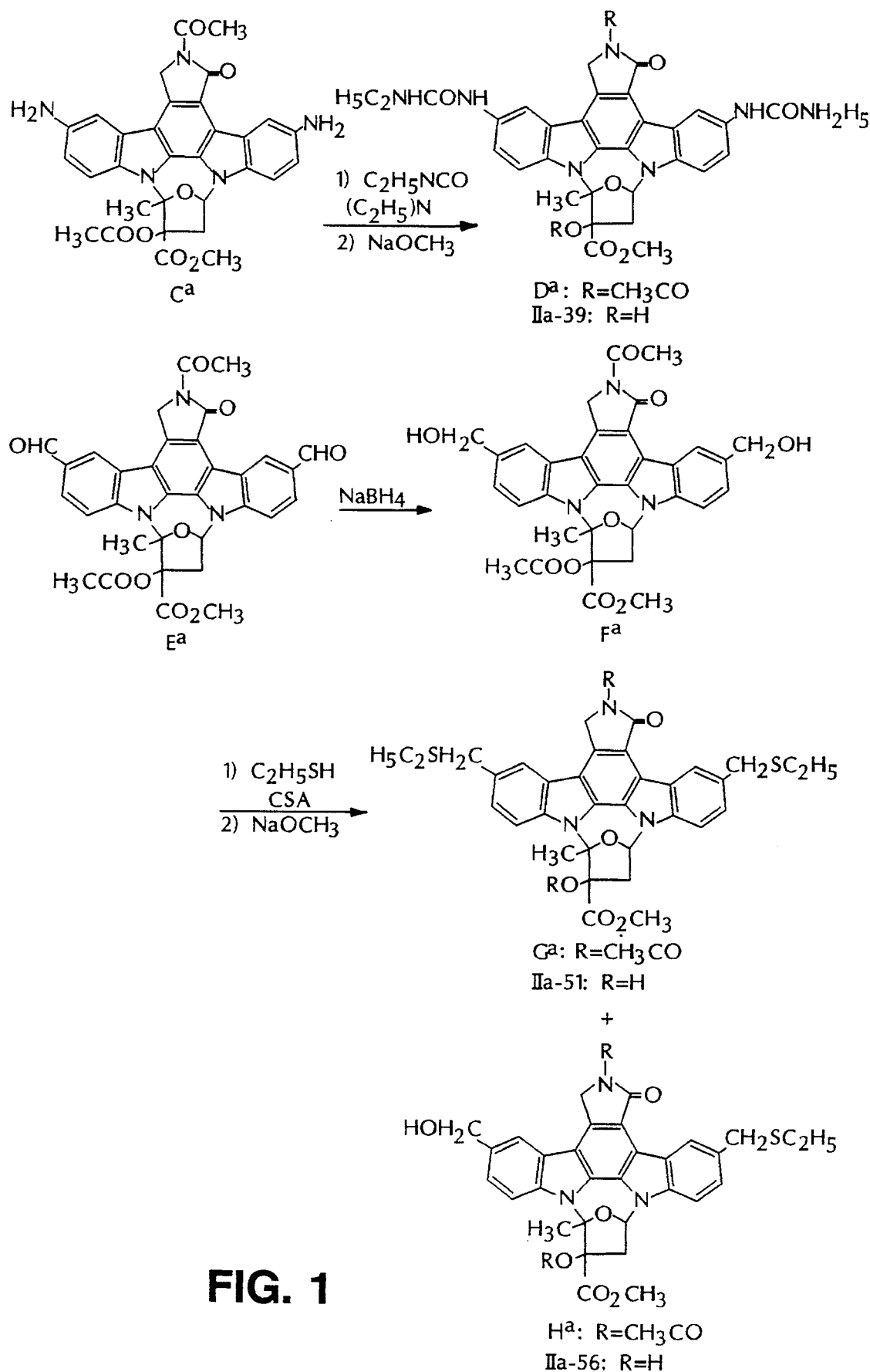
FIG. 1 is a drawing outlining the chemical synthesis of indolocarbazoles $D^a$, IIa-39 $E^a$, $F^a$, $G^a$, IIa-51, $H^a$, and IIa-56.

Aqueous indolocarbazole solutions of the invention are capable of solubilizing an indolocarbazole in order to obtain concentrations of at least 100 μg/ml. Aqueous solutions of the invention are not colloidal and have a number of useful advantages. For example, aqueous solutions of the invention provide: 1) an aqueous solution in which indolocarbazoles are completely solubilized and can be administered at pharmaceutically and biologically useful concentrations of at least 100 μg/ml. Preferably, an aqueous solution will include an indolocarbazole; 2) an aqueous solution allowing filter and heat sterilization; 3) an aqueous solution in which an indolocarbazole can be stored at reduced temperatures for prolonged periods of time at 4° C; and 4) an aqueous non-toxic solution allowing safe intravenous, oral or parenteral administration. These advantages permit convenient and reproducible administration of an indolocarbazole to animals, including humans, and to cell cultures, in a non-toxic, non-colloidal, aqueous solution at physiological pH.

With most pharmaceutical preparations, it is most often the case that the drug is prepared for storage and shipment in a concentrate solution whereby the concentrate solution can subsequently be diluted into appropriate dosage units for pharmaceutical and other biological uses, e.g., subcutaneous, intraperitoneal or intravenous injection of the drug into a human patient. For convenience, the solutions disclosed herein can be considered as comprising two components, the active ingredient, i.e., the indolocarbazole, and the inactive ingredients that make-up the solubilizing solution.

We have determined that for a concentrate (useful for, e.g., shipment or storage of the indolocarbazole), the solubilizing solution comprises between about 1% and 99%, more preferably between about 50% and 99%, and most preferably between about 90% and 99% bwi of a selected organic solvent, with propylene glycol being the most preferred selected organic solvent; and between about 0.25% and about 10% bwi of a dispersant. Thus, our most preferred concentrate comprises between about 90% and 99% bwi of propylene glycol and between about 1% and about 10% bwi of PVP. In the concentrate, the concentration of the indolocarbazole can be at least about 0.5 mg/ml, up to a maximum of about 50 mg/ml. In stability experiments presented in Example 23, we demonstrate that in our most preferred concentrate, the indolocarbazole was not only readily solubilized, but also that the stability of the indolocarbazole was maintained across a variety of temperature extremes for 30 days.

In order to allow for pharmaceutical and biological use of the concentrate, the concentrate can be diluted preferably by using water and PEG. Typically, the diluted solution is utilized relatively quickly, most typically within several hours of dilution. We have determined that a dilute solubilizing solution comprises between about 1% and about 10% bwi of the selected organic solvent, with propylene glycol being the most preferred selected organic solvent; between about 1% and about 10% bwi of a dispersant, with PVP being the most preferred dispersant; between about 1% and about 97%, more preferably between about 30% and about 97%, and most preferably between about 50% and about 97% of water; and between 1% and about 60%, more preferably between about 1% and about 40% and most preferably between about 1% and about 30% bwi of PEG. For dilutions used for intravenous injections, the molecular weight of the PEG is preferably between about 200 and about 400, with a PEG-400 being most preferred. In the diluted solution, the concentration of the indolocarbazole is preferably between 100 μg/ml and about 1 mg/ml.

Other ingredients such as preservatives and the like may be added to the solution.

Preparation of Indolocarbazole Solutions

In general, a solution of the concentrate can be prepared by combining a dispersant such as polyvinylpyrrolidone C-30 and a selected organic solvent such as propylene glycol into a beaker. The mixture is continuously stirred until completely dissolved. Solid PVP or other solution components may take 1–2 hours to dissolve completely at room temperature.

An amount of an indolocarbazole, for example, staurosporine, K-252a, or any one of indolocarbazole A, B, or C (Table 1) can each be individually weighed and added to a small aliquot of the aqueous solution, resulting in a 10 mg/ml solution after the indolocarbazole completely dissolves. Alternatively, a mixture of indolocarbazoles may be combined, weighed, and added to a small aliquot of the aqueous solution resulting in a 10 mg/ml solution after the indolocarbazole completely dissolves. An indolocarbazole solution can be stirred or shaken vigorously overnight. Any undissolved indolocarbazole is removed by standard centrifugation or filtration techniques. The concentration of solubilized indolocarbazole can be determined by reversed phase HPLC using a UV detector (290 nm).

The following HPLC conditions are used to determine the concentration of an indolocarbazole:

| HPLC Buffer Gradient | Buffer | |
|---|---|---|
| | A. | B. |
| 5 min | 65 | 35 |
| 15 min | 35 | 65 |
| 5 min | 35 | 65 |

*Buffer A is 0.1% TFA (trifluoroacetic acid) in water
Buffer B is 0.1% TFA in acetonitrile HPLC Column: Zorbax Rx C-18 4.6×250 mm, 5 micron particle size
Flow Rate: 1 ml/min
Injection volume: 10 μl Prior to injection of an indolocarbazole solution, there is allowed a 10 minute equilibration time. After creating a HPLC buffer gradient, we typically allow a 5 minute wash with 100% buffer B. Indolocarbazole standards for determining the concentration of an indolocarbazole solution can be made by dissolving a known amount of indolocarbazole or a mixture of indolocarbazoles in dimethylsulfoxide (DMSO).

For preparation of the diluted solution, it is preferred that a solution of PEG and water be prepared; additional PVP may be added to this solution. Thereafter, the concentrate can be diluted into the final solution by adding appropriate amounts of the concentrate to the PEG-water-PVP solution.

The invention also features:

A) an aqueous solution including
   i) an indolocarbazole, preferably staurosporine, K-252a, any one of indolocarbazoles A, B, or C (Table 1), or a mixture thereof, at a concentration of at least 0.5 mg/ml;
   ii) between 30% and 60% by weight inclusive of a polyethylene glycol (PEG), preferably any one of PEG-300, PEG-400, PEG-600 or PEG-1000;
   iii) at least one of between 0% and 15% by weight inclusive of polyvinylpyrrolidone (PVP), preferably between 1% and 15% by weight inclusive of PVP; between 0% and 15% by weight of a polyoxyethylene sorbitan fatty acid ester, preferably between 0% and 5% by weight of Tween™ 20 or between 0% and 5% by weight of Tween™ 80, more preferably between 1% and 5% by weight inclusive of Tween™ 20 or between 1% and 15% by weight inclusive of Tween™ 80; between 0% and 15% by weight of a polyethylene glycol 4-isooctylphenyl ether, preferably between 0% and 15% by weight of Triton™ X-100, more preferably between 5% and 15% by weight inclusive of Triton™ X-100; between 0% and 15% by weight of a non-cytotoxic detergent, preferably between 0% and 15% by weight inclusive of either Pluronic™ F68, Pluronic™ L61 or Pluronic™ L64, more preferably between 1% and 5% by weight inclusive of either Pluronic™ F68, Pluronic™ L61 or Pluronic™ L64;
   iv) between 0% and 5% by weight of benzyl alcohol, preferably 1-5% by weight inclusive benzyl alcohol; and v) between 35% and 70% by weight inclusive of water.
B) An aqueous solution including
  (i) an indolocarbazole, preferably staurosporine, K-252a, any one of indolocarbazoles A, B, or C (Table 1), or a mixture thereof, at a concentration of at least 0.5 mg/ml;
  ii) between 30% and 60% by weight inclusive of a polyethylene glycol (PEG), preferably any one of PEG-300, PEG-400, PEG-600 or PEG-1000;
  (iii) and at least one of between 1% and 15% by weight inclusive of PVP; between 1% and 5% by weight inclusive of Tween™ 20, or between 1% and 15% by weight inclusive of Tween™ 80; between 5% and 15% by weight inclusive of Triton™ X-100; between 1% and 5% by weight inclusive of any one of Pluronic™ F68, Pluronic™ L61, or Pluronic™ L64;
  (iv) between 0% and 5% by weight of benzyl alcohol, preferably between 1% and 5% by weight inclusive of benzyl alcohol; and
  (v) between 35% and 70% by weight inclusive of water.
C) An aqueous solution including
  (i) an indolocarbazole, preferably staurosporine, K-252a, any one of indolocarbazoles A, B, or C (Table 1), or a mixture thereof, at a concentration of at least 0.5 mg/ml;
  (ii) between 30% and 60% by weight inclusive of a polyethylene glycol, preferably PEG-400, PEG-600, or PEG-1000;
  (iii) between 1% and 15% by weight inclusive of PVP;
  (iv) between 1% and 5% by weight inclusive of benzyl alcohol; and
  (v) between 35% and 70% by weight inclusive of water.
D) An aqueous solution including
  (i) an indolocarbazole, preferably staurosporine, K-252a, any one of indolocarbazoles A, B or C (Table 1), or a mixture thereof, at a concentration of at least 0.5 mg/ml;
  (ii) between 1% and 10% by weight inclusive of a polyvinylpyrrolidone, preferably with a k value of 17; and
  (iii) between 90% and 99% by weight inclusive of propylene glycol.
E) An aqueous solution including
  (i) an indolocarbazole, preferably staurosporine, K-252a, any one of indolocarbazoles A, B or C (Table 1), or a mixture thereof, at a concentration between 100 µg/ml and 1 mg/ml;
  (ii) between 1% and 30% by weight inclusive of a polyethylene glycol having an average molecular weight between 200 and 400 inclusive;
  (iii) between 1% and 10% by weight inclusive of propylene glycol;
  (iv) between 1% and 10% by weight inclusive of a polyvinylpyrrolidone, preferably with a k value of 17; and
  (v) between 50% and 97% by weight inclusive of water.

Each example described below is summarized in Table 2.

EXAMPLE 1

Fifty g of PEG-400 were added to 50 ml of water and the mixture vigorously stirred until completely dissolved. One mg of either K-252a, staurosporine or the indolocarbazoles B or C (see Table 1) were added individually to a 100 µl aliquot of the PEG-400 solution and the resulting mixture was shaken overnight. The solution was clarified by centrifugation at 1000 rpm for 10 minutes. The supernatant was saved and any residue discarded. Ten µl of the supernatant was removed, diluted with DMSO (100:1) and the concentration of dissolved K-252a determined by HPLC.

EXAMPLE 2

Same as example 1 except that PEG-600 was used instead of PEG-400.

EXAMPLE 3

Same as example 1 except that PEG-1000 was used instead of PEG-400.

EXAMPLE 4

Same as example 1 except that 48 ml of water was used and 2 g of benzyl alcohol was added to the PEG-400 solution.

EXAMPLE 5

Same as example 2 except that 48 ml of water was used and 2 g of benzyl alcohol was added to the PEG-600 solution.

EXAMPLE 6

Same as example 3 except that 48 ml of water was used and 2 g of benzyl alcohol was added to the PEG-1000 solution.

EXAMPLE 7

2.5 g of benzyl alcohol was added to 47.5 g of PEG-400 and, in a separate container, 2.5 g of Pluronic F68 was added to 47.5 ml of water. Each solution was stirred until completely dissolved, then each solution was combined and stirred until homogeneous. One mg of K-252a was added to 100 µl of the solution and the resulting mixture was shaken overnight. The solution was clarified by centrifugation at 1000 rpm for 10 minutes. Ten (10) µl of supernatant was removed, diluted with DMSO (100:1), and the concentration of dissolved K-252a determined by HPLC.

EXAMPLE 8

Same as example 7 except that Pluronic™ L61 was used instead of Pluronic™ F68.

EXAMPLE 9

Same as example 7 except that Pluronic™ L64 was used instead of Pluronic™ F68.

EXAMPLE 10

Same as example 7 except that Tween™ 20 was used instead of Pluronic™ F68.

EXAMPLE 11

Same as example 7 except that Tween™ 80 was used instead of Pluronic™ F68.

EXAMPLE 12

Same as example 7 except that PVP was used instead of Pluronic™ F68 and PEG-300 was used instead of PEG-400.

EXAMPLE 13

Same as example 12 except that PEG-400 was used instead of PEG-300 and indolocarbazoles A, B or C were each solubilized individually in addition to K-252a.

EXAMPLE 14

Same as example 12 except that PEG-600 was used instead of PEG-300 and indolocarbazoles A, B or C were each solubilized individually in addition to K-252

EXAMPLE 15

Same as example 12 except that PEG-1000 was used instead of PEG-300.

EXAMPLE 16

Ten (10) g of Triton X-100 was added to 38 ml of water and the mixture was stirred thoroughly. After the Triton X-100 was dissolved, 50 g of PEG-600 and 2 g of benzyl alcohol was added and the resulting mixture was stirred until homogeneous. One mg of K-252a, indolocarbazole C or staurosporine was each added individually to 100 µl of the solution and the three solutions shaken overnight. The solutions were clarified by centrifugation at 1000 rpm for 10 minutes. The supernatant was saved and any residue discarded. Ten (10) µl of supernatant were removed, diluted with DMSO (100:1), and the concentration of dissolved indolocarbazole determined by HPLC.

EXAMPLE 17

Same as example 16 except that Tween™ 80 was used instead of Triton™ X-100.

EXAMPLE 18

Same as example 16 except that PVP was used instead of Triton™ X-100.

EXAMPLE 19

Ten (10) g of PVP was added to 48 ml of water and the mixture was stirred until the PVP was completely dissolved. Forty (40) g of PEG-1000 and 2 g of benzyl alcohol was added and the mixture was stirred until the resulting solution was homogeneous. One (1) mg of K-252a, indolocarbazole A, B or C (Table 1) was each added individually to a 100 µl aliquot of the solution and shaken overnight. The solution was clarified by centrifugation at 1000 rpm for 10 minutes. The supernatant was saved and any residue discarded. Ten 10 µl of supernatant was removed, diluted with DMSO (100:1), and the concentration of indolocarbazole determined by HPLC.

Example 20–22, below and in Table 2 show the saturation levels obtainable by dissolving any one of K-252a, staurosporine, or indolocarbazoles A, B, or C in aqueous solutions of the invention.

EXAMPLE 20

Same as example 14 except that 10 mg of K-252a, or any one of indolocarbazole A, B, or C (Table 1) were each added individually to the solution.

EXAMPLE 21

Same as example 15 except that 10 mg of K-252a or indolocarbazole C (Table 1) was each added individually to the solution.

EXAMPLE 22

Same as example 18 except that 10 mg of K-252a, staurosporine or indolocarbazole B or C (Table 1) was each added individually to the solution.

EXAMPLE 23

In a flask, 10 g of PVP (k value of 17) was added to 990 grams of propylene glycol. This mixture was stirred until the PVP was completely dissolved. Two hundred fifty (250) mg of compound A (Table 1) was added to 10 ml of the above solution and the mixture was stirred until compound A was completely dissolved. This solution is called Indolocarbazole Propylene Glycol Concentrate (IPGC).

To test for the stability of an indolocarbazole in this solution, 1 ml aliquots of IPGC were removed and placed in small amber colored vials and kept at 4° C room temperature (about 25° C.), 37° C, and 60° C for 4, 7, 14 and 30 days. The sample at 4° C was kept in a refrigerator and received light when a door was opened. The sample at room temperature was placed on the laboratory bench and exposed to the fluorescent lights of the room during the day. The samples at 37° C and 60° C were kept in small incubators essentially in the dark. A 1 ml aliquot of the same IPGC was added to a clear vial and that vial was kept at 25° C in 300 foot candles of light for 4, 7, 14 and 30 days. At each interval of time, an aliquot of IPGC was removed from each vial, diluted 200 fold in DMSO and the concentration of compound A determined by reversed phase HPLC using a UV detector (290 nm). The results (Table 3) show that when shielded from bright light (in the amber vials), compound A is completely stable in IPGC for at least 30 days at temperatures between 4° C. and 60° C., but when it is exposed to 300 foot candles of light, compound A loses some activity (i.e., loss of 13.3%) in 30 days.

For pharmaceutical and other biological uses, IPGC can be diluted to any desired concentration of indolocarbazole by adding the required amount of IPGC to any of the solutions listed in Table 2. However, for the intravenous administration to animals and man IPGC is preferably diluted in Indolocarbazole Diluent Solution.

In this example, compound A was further diluted in Indolocarbazole Diluent Solution. Indolocarbazole Diluent Solution was prepared by adding 300 grams of polyethylene glycol 400 to a beaker. Ten (10) g of PVP (k value of 17) was added to the beaker and the mixture was stirred until the PVP was dissolved. Six hundred ninety (690) ml of water was then added and the resulting mixture was stirred until all the components were in solution.

An Indolocarbazole Propylene Glycol Concentrate solution containing 25 mg/ml of compound A was diluted 25 fold in Indolocarbazole Diluent Solution resulting in an administration solution containing 1 mg/ml of compound A, 30% polyethylene glycol 400, 4% propylene glycol, 1.04% PVP (k value 17), and 64.96% water. This solution had a pH of 4.5. Compound A lost only 0.3% of its a concentration when kept in amber vials for 4 days at room temperature exposed to the fluorescent lights of the laboratory during the day.

TABLE 1

Indolocarbazoles A, B, and C

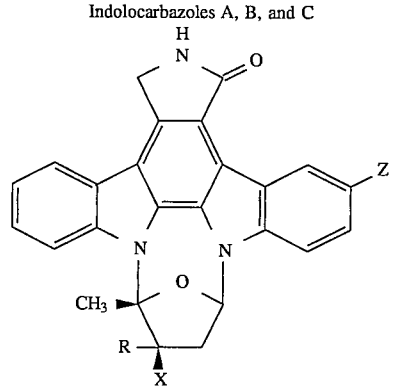

| Indolocarbazole | R | X | Z |
|---|---|---|---|
| A | $OCH_3$ | $CH_2OH$ | H |
| B | OH | $CO_2CH_3$ | OH |
| C | OH | $CO_2CH_3$ | $CH_2SOCH_2CH_3$ |

Materials

The aqueous solutions of the invention were made with U.S.P. grade materials. Tween™ 20 (lot #33H0250) and Triton™ X-100 (lot #41HO426) were obtained from Sigma Chemical Company, P.O. Box 14508, St. Louis, Mo. 63178. Pluronic™ L61 (lot #GB146), Pluronic™ L64 (lot #GE306), Pluronic™ F68 (lot #EF343), PEG 1000 (lot #HL282), PEG 600 (lot #EF114), PEG 400 (lot #HK096), PEG 300 (lot #HH280), and Tween™ 80 (lot #EF276) and benzyl alcohol were obtained from Spectrum Chemical Mfg. Corp., 755 Jersey Avenue, New Brunswick, N.J. 08901-3605. Polyvinylpyrrolidone C-30 (lot #TX01211) was obtained from International Specialty Products, 1361 Alps Road, Wayne, N.J. 07470.

Synthesis of Preferred Indolocarbazoles

An indolocarbazole is capable of being solubilized by an aqueous solution of the invention. The synthesis of preferred indolocarbazoles is described below. K-252a and staurosporine are commercially available from Kamiya Biomedical.

TABLE 2

Examples

| Example | | K252a | Compound A | Compound B | Compound C | Staurosporine |
|---|---|---|---|---|---|---|
| | Target - 10 mg/ml in | | | | | |
| 1 | 50% PEG 400, 50% H2O | 1.39 | — | 3.15 | 0.75 | 0.71 |
| 2 | 50% PEG 600, 50% H2O | 1.92 | — | 2.68 | 0.50 | 1.89 |
| 3 | 50% PEG 1000, 50% H2O | 1.82 | — | 4.44 | 0.72 | 1.65 |
| 4 | 50% PEG 400, 2% BA, 48% H2O | 2.08 | — | 3.26 | 1.01 | 1.21 |
| 5 | 50% PEG 600, 2% BA, 48% H2O | 2.72 | — | 3.59 | 0.89 | 1.89 |
| 6 | 50% PEG 1000, 2% BA, 48% H2O | 1.83 | — | 5.02 | 0.8 | 1.68 |
| 7 | 47.5% PEG 400, 2.5% BA, 2.5% Pluronic F68, 47.5% H2O | 5.5 | — | — | — | — |
| 8 | 47.5% PEG 400, 2.5% BA, 2.5% Pluronic L61, 47.5% H2O | 3.5 | — | — | — | — |
| 9 | 47.5% PEG 400, 2.5% BA, 2.5% Pluronic L64, 47.5% H2O | 1.8 | — | — | — | — |
| 10 | 47.5% PEG 400, 2.5% BA, 2.5% Tween 20, 47.5% H2O | 6.0 | — | — | — | — |
| 11 | 47.5% PEG 400, 2.5% BA, 2.5% Tween 80, 47.5% H2O | 3.7 | — | — | — | — |
| 12 | 47.5% PEG 300, 2.5% BA, 2.5% PVP, 47.5% H2O | 9.6 | — | — | — | — |
| 13 | 47.5% PEG 400, 2.5% BA, 2.5% PVP, 47.5% H2O | 10* | 10 | 10* | 4.0 | — |
| 14 | 47.5% PEG 600, 2.5% BA, 2.5% PVP, 47.5% H2O | 10 | 10 | 10 | 4.6 | — |
| 15 | 47.5% PEG 1000, 2.5% BA, 2.5% PVP, 47.5% H2O | 10 | — | — | — | — |
| 16 | 50% PEG 600, 2% BA, 10% Triton X-100, 38% H2O | 10 | — | — | 4.63 | 7.59 |
| 17 | 50% PEG 600, 2% BA, 10% Tween 80, 38% H2O | 8.83 | — | — | 4.79 | 4.6 |
| 18 | 50% PEG 600, 2% BA, 10% PVP, 38% H2O | 10 | — | — | 4.59 | 8.41 |
| 19 | 40% PEG 1000, 2% BA, 10% PVP, 48% H2O | 10 | 10 | 10 | 6.0 | — |
| | Saturation levels in | | | | | |
| 20 | 47.5% PEG 600, 2.5% BA, 2.5% PVP, 47.5% H2O | 10 | 40 | 10 | 4.6 | — |
| 21 | 47.5% PEG 1000, 2.5% BA, 2.5% PVP, 47.5% H2O | 14.1 | — | — | 5 | — |
| 22 | 50% PEG 600, 2% BA, 10% PVP, 38% H2O | 21.2 | — | 16.4 | 4.6 | 8.4 |

Concentration Obtained in mg/ml / * precipitates form after 24 hours

TABLE 3

Stability of Compound A in Indolocarbazole Propylene Glycol Concentrate

| Time | 4° C. | Room Temp. | 37° C. | 60° C. | Clear vial |
|---|---|---|---|---|---|
| 0 | 100% | 100% | 100% | 100% | 100% |
| 4 days | 100% | 100% | 100% | 100% | 99.1% |
| 7 days | 100% | 100% | 100% | 100% | 98.7% |
| 14 days | 100% | 100% | 100% | 100% | 95.1% |
| 30 days | 100% | 100% | 100% | 100% | 86.7% |

I. Synthesis of Bis-N-Substituted Staurosposine Derivatives 1,6-Hexamethylene-bis-(carbamylstaurosporine) (HBCS)

A solution of 1.0 mg (2.15 micromoles) of staurosporine (Kamiya Biomedical Company, Thousand Oaks, Calif.) in 1.00 ml of ethyl acetate (dried over anhydrous magnesium sulfate) was treated with 17 microliters (1.08 micromoles) of a solution of 10.75 mg of hexamethylene-bis-isocyanate in 1.0 ml of dried ethyl acetate. The reaction mixture in an amber glass reaction vial was allowed to stand at room temperature for two days. A crystalline deposit weighing 600 micrograms was separated. Its composition was verified by fast atom bombardment mass spectroscopy (FAB-MS).
M+H⁺ Calculated=1102 M+Na⁺ Calculated=1124
Found=1102 Found=1124

This product and all of the subsequently described staurosporine derivatives were stored in non-actinic glass vials.

p-Phenylene-bis-(carbamylstaurosporine) (PBCS)

A solution of 1.0 mg. of staurosporine (2.15 micromoles) in 1.00 ml of dried ethyl acetate was treated with 45 microliters (1.08 micromoles) of a solution prepared from 3.83 mg of p-phylene diisocyanate (Trans World Chemicals P1586-1) in 1.00 ml of dried ethyl acetate. The reaction mixture was allowed to stand overnight. A white precipitate deposited. Then 0.5 ml of petroleum ether was added. The mixture was filtered into a vacuum-dried sintered-glass funnel. A total of 0.90 mg of crystalline product was collected and was identified as p-phenylene-bis-(carbamylstaurosporine) by fast atom bombardment mass spectroscopy.
M+H⁺ Calculated=1093 Found=1093

N-Phenylcarbamylstaurosporine (PCS)

A solution of 2.0 mg of staurosporine (4.30 micromoles) in 1.50 ml of dried ethyl acetate was treated with 468 μl (4.30 micromoles) of a solution of 10 μl of phenyl isocyanate in 0.990 ml of dried ethyl acetate. The solution was allowed to stand overnight and 3 ml of hexade was added in portions. Colorless crystals were obtained which weighed 2.39 mg. After recrystallizing this product from 1 ml of ethyl acetate and 2 ml of petroleum ether, 1.75 mg of a crystalline product was isolated. From a similar preparation, the product's composition as N-phenylcarbamylstaurosporine was verified by FAB-MS.
M+H⁺ Calculated=586
Found=586

N-Phenylthiocarbamylstaurosporine (PTCS)

A solution of 1.0 mg (2.15 micromoles) of staurosporine in 1.00 ml of ethyl acetate was treated with 26 microliters of a stock solution of 10 microliters of phenyl isothiocyanate in 1.00 ml of ethyl acetate. This aliquot contained 290 micrograms (2.15 micromoles) of phenyl isothiocyanate. The reaction mixture was held at 25° C. overnight, and then 2.0 ml of hexade was added. The resulting crystalline product was filtered off, washed with hexade and dried with a stream of argon gas.
FAB-MS Calc: M+H⁺=602
Found=602

N-Ethylcarbamylstaurosporine (ECS)

A solution of 0.9 mg (1.93 micromoles) of staurosporine in 900 microliters of ethyl acetate was treated with 1.93 micromoles (30.2 microliters of a stock solution of 9.05 mg of ethyl isocyanate in 2.00 ml of dried ethyl acetate) of ethyl isocyanate. The reaction mixture was held at 25° C overnight, and 2.0 ml of hexane was added. The crystalline product was separated and dried.

FAB-MS Calc.: M+H⁺=538 M+Na⁺=560
Found=538 =560

II. Synthesis of K-252a Derivatives

K-252a derivatives described below are indolocarbazoles. Preferred K-252a derivatives may be represented by formulae IIa, IIIa, and IVa shown below:

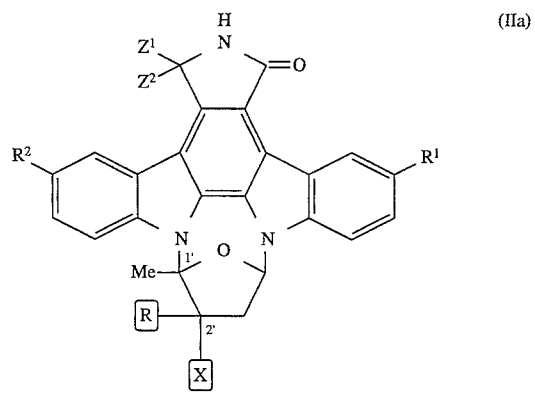

(IIa)

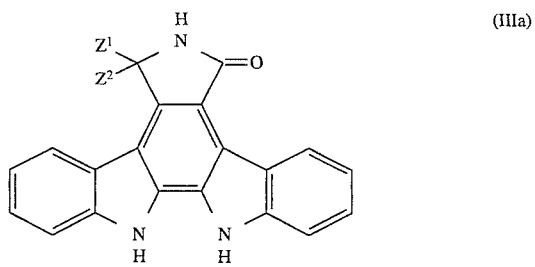

(IIIa)

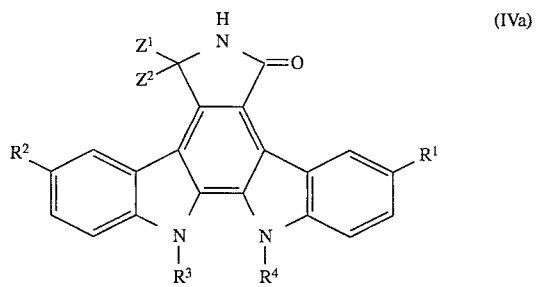

(IVa)

with substitutions shown in Table 4, below. The K-252a derivatives may be prepared de novo by chemical synthesis using methods known to those skilled in the art. For example, procedures used for preparation of Derivative IIa are described by Murakata et al (U.S. Pat. No. 4,923,986). Procedures used for preparation of Derivative IIIa are described by Moody et al., *J. Org. Chem.* 57:2105–2114 (1992); Steglich et al., *Angew. Chem. Int. Ed. Engl.* 19:459–460 (1980); Nakanishi et al., *J. Antibiotics* 39:1066–1071 (1986); and Japanese Patent Application No. 60-295172 (1985). Further methods are described for Derivatives IIa-1, 9, 12 and 15 in Japanese Patent Application No. 60-295173 (1985); Derivatives IIa-2, 3, 4, 24, 25 and 26 in Japanese Patent Application No. 62-327858 (1987); Derivatives IIa-20 in Japanese Patent Application No. 62-327859 (1987); and Derivatives IIa-10 in Japanese Patent Application No. 60-257652 (1985) by Meiji Seika Kaisha Ltd. Compounds not disclosed below may be found in these references.

TABLE 4

Derivatives of K-252a[10]

| Derivative | $R^1$ | $R^2$ | X | R | $Z^{1[1]}$ $Z^2$ |
|---|---|---|---|---|---|
| IIa-1 | H | H | $CH_2N_3$ | OH | H |
| IIa-2 | $NHCONHC_6H_5$ | H | $CO_2CH_3$ | OH | H |
| IIa-3 | $CH_2SOC_2H_5$ | H | $CO_2CH_3$ | OH | H |
| IIa-4 | H | H | $CH_2OH$ | $OCH_3$ | H |
| IIa-5 | H | H | $CONHC_2H_5$ | OH | H |
| IIa-6 | H | H | CH=NNH— | OH | H |
| IIa-7[2,7] | H | H | $CH_2NH$—Gly | OH | H |
| IIa-8 | H | H | $CON(CH_3)_2$ | OH | H |
| IIa-9[3] | H | H | —$CH_2NHCO_2$— | | H |
| IIa-10 | Br | H | $CO_2CH_3$ | OH | H |
| IIa-11 | H | H | $CONH_2$ | OH | H |
| IIa-12 | H | H | $CH_2OH$ | OH | H |
| IIIa-1 | — | — | — | — | H |
| IIa-13 | H | H | $CONHC_3H_7$ | OH | H |
| IIa-14[2] | H | H | $CH_2NH$—Ser | OH | H |
| IIa-15 | H | H | $CH_2SOCH_3$ | OH | H |
| IIa-16 | H | H | CH=NOH | OH | H |
| IIa-17 | H | H | CON O | OH | H |
| IIa-18[2,7] | H | H | $CH_2NH$—Pro | OH | H |
| IIa-19 | H | H | $CH=NNHC(=NH)NH_2$ | OH | H |
| IIa-20 | Br | Br | $CO_2CH_3$ | OH | O |
| IIa-21 | H | H | $CONH(CH_2)_2OH$ | OH | H |
| IIa-22 | H | H | $CO_2CH_3$ | OH | O |
| IIIa-2 | — | — | — | — | O |
| IIa-23 | H | H | H | OH | H |
| IIa-24 | H | H | $CH=NNHCONH_2$ | OH | H |
| IIa-25 | H | H | $CH_2OCOCH_3$ | OH | H |
| IIa-26[3] | H | H | —$CH_2OC(CH_3)_2O$— | | H |
| IIa-29 | $NHCONHC_2H_5$ | H | $CO_2CH_3$ | OH | H |
| IIa-30 | $CH_2SC_2H_5$ | H | $CO_2CH_3$ | OH | H |
| IIa-31 | Br | H | $CH_2OH$ | OH | H |
| IIa-32 | Br | Br | $CO_2CH_3$ | OH | H |
| IIa-33 | $CH_2SC_6H_5$ | H | $CO_2CH_3$ | OH | H |
| IIa-34 | Cl | Cl | $CO_2CH_3$ | OH | H |
| IIa-36 | H | H | $CONHC_6H_5$ | OH | H |
| IIa-37 | H | H | $CH_2SO$ | OH | H |
| IIa-38 | H | H | $CH_2NHCO_2C_6H_5$ | OH | H |
| IIa-39 | $NHCONHC_2H_5$ | $NHCONHC_2H_5$ | $CO_2CH_3$ | OH | H |
| IIa-40 | $N(CH_3)_2$ | H | $CO_2CH_3$ | OH | H |
| IIa-41 | $CH_3$ | H | $CO_2CH_3$ | OH | H |
| IIa-42 | $CH_2OCONHC_2H_5$ | H | $CO_2CH_3$ | OH | H |
| IIa-43 | $NHCO_2CH_3$ | H | $CO_2CH_3$ | OH | H |
| IIa-44 | Br | Br | $CH_2OH$ | OH | H |
| IIa-45 | Br | Br | $CONHC_6H_5$ | OH | H |
| IIa-46 | Br | Br | $CONHCH_2CH_2OH$ | OH | H |
| IIa-47 | $CH_2OC_2H_5$ | H | $CO_2CH_3$ | OH | H |
| IIa-48 | $CH_2N(CH_3)_2$ | H | $CO_2CH_3$ | OH | H |
| IIa-49 | $CH_2SO_2C_2H_5$ | H | $CO_2CH_3$ | OH | H |
| IIa-50 | $CH_2S$ | H | $CO_2CH_3$ | OH | H |
| IIa-51 | $CH_2SC_2H_5$ | $CH_2SC_2H_5$ | $CO_2CH_3$ | OH | H |
| IIa-52 | CH=NNH | H | $CO_2CH_3$ | OH | H |
| IIa-53 | $CH_2S$ | H | $CO_2CH_3$ | OH | H |
| IIa-54 | $CH_2S(O)$ | H | $CO_2CH_3$ | OH | H |
| IIa-55 | $CH_2S(O)$ | H | $CO_2CH_3$ | OH | H |
| IIa-56 | $CH_2SC_2H_5$ | $CH_2OH$ | $CO_2CH_3$ | OH | H |
| IIa-57 | H | H | $CH_2NHCO_2CH_3$ | OH | H |
| IIa-58 | Br | H | $CONH_2$ | OH | H |
| IIa-59 | H | H | $CH_2SC_6H_5$ | OH | H |
| IIa-60 | H | H | $CH_2S$ | OH | H |
| IIa-61 | H | H | $CH_2SOC_6H_5$ | OH | H |
| IVa-1[4,9] | H | H | — | — | H |
| IVa-2[5] | Br | H | — | — | H |
| IVa-3[6] | H | H | — | — | H |
| IVa-4[8,9] | H | H | — | — | H |

[1]$Z^1$ and $Z^2$ are both hydrogen, or both are combined together to represent oxygen, where indicated.
[2]NH-amino acid linkage is an amide bond through the carboxyl group of the amino acid.
[3]X and R are combined together to form the linking group.
[4]$R^3$ is $CH_2CH=CH_2$; $R^4$ is H.
[5]$R^3$ and $R^4$ are each H.
[6]$R^3$ and $R^4$ are each $CH_2CH=CH_2$.
[7]Compound is in the form of the hydrochloride.
[8]$R^3$ is H and $R^4$ is $CH_2CH=CH_2$.
[9]IVa-1 and IVa-4 is a 1.5 to 1.0 mixture of the two components.
[10]K-252a is represented by $R^1 = R^2 = H$, $X = CO_2CH_3$, $R = OH$, $Z^1$ and $Z^2 = H$.

1) Derivative IIa-4

Compound $A^a$ (962 mg, 2 mmol) was dissolved in a mixture of 30 ml of tetrahydrofuran and 10 ml of methanol, and then 760 mg of sodium borohydride (20 mmol) was added thereto under ice cooling, followed by stirring at the same temperature for 4 hours and further at room temperature for 12 hours. After 3N hydrochloric acid was added thereto, the solution was washed with an aqueous solution of sodium chloride and dried over magnesium sulfate, followed by evaporation of the solvent. The residue was purified by silica gel column chromatography (chloroform/methanol= 98/2) to give 882 mg (yield 97%) of Derivative IIa-4.

Melting Point: 130°–140° C.

$^1$H-NMR (DMSO-$d_6$) δ(ppm): 2.032 (1H, dd, J=5.0, 13.9 Hz), 2.231 (3H, s), 2.967(3H, s), 3.609(1H, dd, J=7.6, 13.4 Hz), 3.959(2H, m), 5.000(2H, s), 5.268(1H, t, J=5.3 Hz), 7.065(1H, dd, J=4.9, 7.3 Hz), 7.254–8.038 (7H, m), 8.565(1H, s), 9.206 (1H, d, J=7.8 Hz)

Compound $A^a$

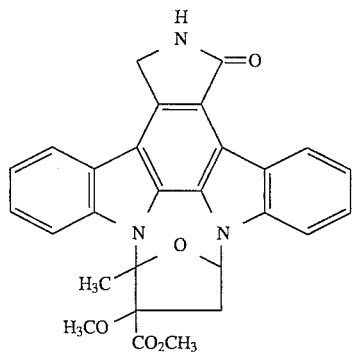

2) Derivative IIa-14

Compound $B^a$ (393 mg, 0.9 mmol) was dissolved in 25 ml of tetrahydrofuran, and then 3 ml of tetrahydrofuran containing 309 mg of carbobenzoxy-L-serine (1.35 mmol), 156 mg of N-oxysuccinimide (1.35 mmol), 0.1 ml of 4-methylmorpholine (0.9 mmol) and 279 mg of dicyclohexylcarbodiimide (1.35 mmol) was added under ice cooling, followed by stirring for 12 hours. The reaction mixture was filtered and the solvent was evaporated. The residue was purified by silica gel column chromatography (chloroform/methanol= 99/1) to give 429 mg (yield 72%) of Compound $C^a$.

Melting Point: 188°–193° C.

SIMS (m/z): 660 (M+1)$^+$

Compound $C^a$ (399 mg) was dissolved in 10 ml of dimethylformamide, and then 300 mg of 10% palladium on carbon was added, followed by stirring at 50° C for 7 hours in a hydrogen stream. The reaction mixture was filtered through Celite and the solvent was evaporated. The residue was purified by silica gel column chromatography (chloroform/methanol/28% ammonium hydroxide=90/10/1) and the obtained product was dissolved in 5 ml of tetrahydrofuran, followed by addition of 5 ml of 1.7N hydrogen chloride/ethyl acetate and 10 ml of diethyl ether. The precipitate was separated from the solution by filtration to give 234 mg (yield 69%) of Derivative IIa-14.

Melting Point: >300° C.

$^1$H-NMR (DMSO-$d_6$+$D_2$O) δ(ppm): 1.92–2.28(1H, m), 2.20 (3H, s), 2.84–3.12(7H, m), 3.40–4.20(5H, m), 5.04 (2H, s), 6.98(1H, m), 7.24–8.20(7H, m), 8.76(1H, brs), 9.22(1H, d, J=8Hz)

SIMS (m/z ): 527 (M+2)$^+$

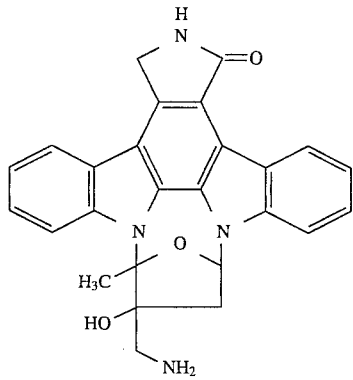

Compound $B^a$

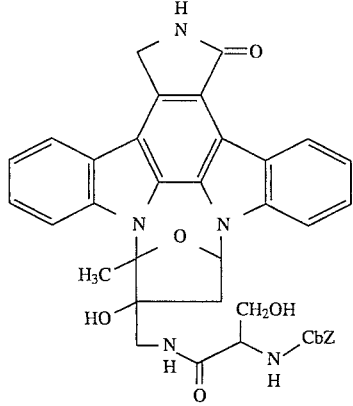

Compound $C^a$

CbZ: carbobenzoxy

3) Derivative Va-1

Derivative Va-1, in which $R^1$ is $CH_2SO_2R^7$ and X is $CO_2R^5$ can be prepared by the following reaction step:

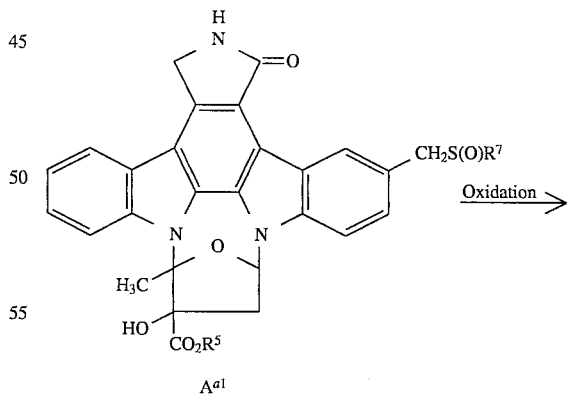

$A^{a1}$

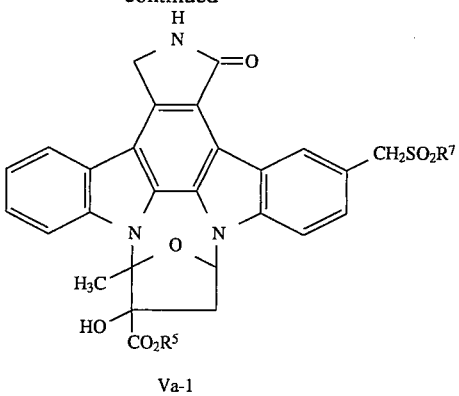

Va-1

($R^5$ represents lower alkyl or $CH_2NHCO_2R^6$ in which $R^6$ represents lower alkyl or aryl; $R^7$ represents lower alkyl.)

Derivative Va-1 can be obtained by treatment of Compound ($A^{a1}$) with 1 to 1.5 equivalents of an oxidant. An example of the oxidant is m-chloroperbenzoic acid. As a reaction solvent, a halogenated hydrocarbon such as methylene chloride, chloroform, or ethylene dichloride, or the like is used. The reaction is completed in 0.5 to 1 hour at $-20°$ to $30°$ C.

The starting compound ($A^{a1}$) is disclosed in Japanese Published Unexamined Patent Application No. 295588/88.

4) Derivative Va-2

Derivative Va-2 in which $R^1$ is hydrogen and X is $CH_2NHCO_2R^6$ can be prepared by the following reaction step:

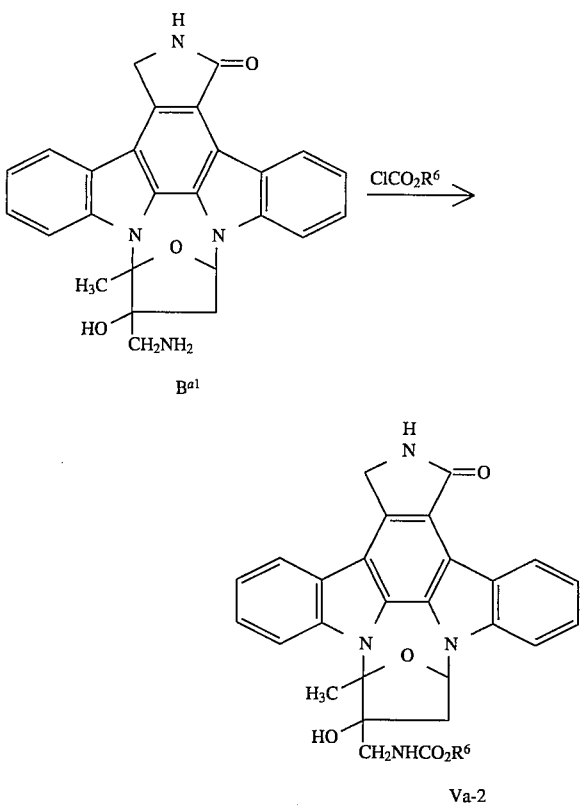

$R^6$ represents lower alkyl or aryl.

Derivative Va-2 can be obtained by reaction of Compound ($B^{a1}$) with 1 to 3 equivalents $ClCO_2R^6$ in the presence of 1 to 3 equivalents of a base. An example of the base is triethylamine. As a reaction solvent, a halogenated hydrocarbon such as methylene chloride, chloroform, or ethylene dichloride, or the like is used. The reaction is completed in 0.5 to 3 hours at $-10°$ to $30°$ C.

The starting compound ($B^{a1}$) is disclosed in Japanese Published Unexamined Patent Application No. 155285/87 (hereby incorporated by reference).

5) Derivative IIa-49

Compound A-1 in which $R^5$=CH and $R^7$=$CH_5$ of compound $A^{a1}$ (above) (27 mg, 0.05 mmol) was dissolved in 1 ml of chloroform, and then 10 mg (0.06 mmol) of m-chloroperbenzoic acid was added thereto under ice cooling, followed by stirring at the same temperature for 45 minutes. After dilution with chloroform, the mixture was washed successively with a 8% aqueous solution of sodium thiosulfate, a saturated aqueous solution of sodium bicarbonate, water, and a saline solution, and dried over sodium sulfate. After evaporation of the solvent, the residue was subjected to silica gel column chromatography (chloroform/methanol=95/5) to give 17.7 mg (yield 62%) of Derivative IIa-49.

$^1$H-NMR (DMSO-$d_6$) δ(ppm): 1.298(3H, t, J=7.5 Hz), 2.037 (1H, dd, J-5.0, 14.1 Hz), 2.153(3H, s), 3.096(2H,q, J=7.5 Hz), 3.266 (2H, s), 3.929(3H, s), 4.985 (1H, d, J=17.0 Hz), 5.043(1H, d, J=17.0 Hz), 6.348(1H, s), 7.147 (1H, dd, J=4.9, 7.1 Hz), 7.345–8.070(6H, m), 8.612(1H, s), 9.232(1H, d, J=1.5 Hz)

FAB-MS (m/z): 574 (M+1)$^+$

6) Derivative IIa-57

Compound ($B^{a1}$) (43.8 mg, 0.1 mmol) was dissolved in 1 ml of tetrahydrofuran, and then 9.3 μl (0.12 mmol) methyl chloroformate and 28 μl (0.2 mmol) of triethylamine were added thereto, followed by stirring for 50 minutes under ice cooling. After dilution with tetrahydrofuran, the mixture was washed with a saline solution, and dried over sodium sulfate. After evaporation of the solvent, the residue was subjected to silica gel column chromatography (chloroform/methanol=99/1) to give 32.6 mg of Derivative IIa-57.

$^1$H-NMR (CDCl$_3$) δ(ppm): 2.099(3H, s), 2.679(1H, m), 3.204(1H, dd, J=6.7m 13.8 Hz), 3.837(3H, s), 4.446 (1H, d, J=17.3 Hz), 4.634 (1H, d, J=17.6 Hz), 5.497 (1H, brs), 6.591(1H, brs), 7.010–8.037(7H, m), 8.592(1H, d, J=6.6 Hz)

FAB-MS (m/z): 497 (M+1)$^+$

7) Derivative IIa-38

Substantially the same procedure as in the preparation of Derivative IIa-57 was repeated using 43.8 mg (0.1 mmol) of Compound ($B^{a1}$) and 15 μl of phenyl chloroformate to give 27.8 mg (yield 50%) of Derivative IIa-38.

$^1$H-NMR (CDCl$_3$) δ(ppm): 2.111(3H, s), 2.890(1H, brd, J=13.7 Hz ), 3.262 ( 1H, dd, J=7.5, 13.9 Hz ), 3.742(1H, d, J=13.4 Hz), 3.967(1H, d, J=12.9 Hz), 4.582(1H, d, J=16.3 Hz), 5.342(1H, brs), 5.906(1H, brs), 6.550 (1H, brs), 7.005–8.042(12H, m), 8.596(1H, d, J=7.6 Hz)

FAB-MS (m/z): 559 (M+1)$^+$

8) Derivative IIa-39

Compound ($C^a$) (Japanese Published Unexamined Patent Application No. 295588/88) (20 mg, 0.035 mmol) was dissolved in 1 ml of chloroform, and then 14.6 μl (0.105 mmol) of triethylamine and 13.9 μl (0.175 mmol) of ethyl isocyanate were added thereto, followed by stirring at room temperature for 2 hours. To the solution was added 1 ml of methanol, followed by dilution with chloroform. The mixture was washed successively with water and a saline solution, and dried over sodium sulfate. After evaporation of the solvent, the residue was subjected to silica gel column chromatography (chloroform/methanol=98/2) to give 21 mg (yield 84% of Compound ($D^a$).

$^1$H-NMR (CDCl$_3$) δ(ppm): 1.195(3H, t, J=7.2 Hz), 1.222(3H, t, J=7.2Hz), 1.664(3H, s), 2.194(3H, s), 2.555(3H, s), 3.346(4H, q, J=7.2 Hz), 3.820(1H, dd, J=7.5, 14.6 Hz), 3.938(3H, s), 5.036(1H, d, J=17.7 Hz), 5.125(1H, d, J=17.2 Hz), 6.745(1H, dd, J=4.8, 7.4 Hz), 7.260–7.898(5H, m), 8.690(1H, d, J=1.9 Hz)

FAB-MS (m/z): 724 (M+1)$^+$

Compound (D$^a$) (9 mg, 0.012 mmol) was dissolved in a mixture of 0.2 ml of tetrahydrofuran and 0.2 ml of methanol, and then 2 μl of 28% sodium methoxide/methanol was added thereto, followed by stirring at room temperature for 10 minutes. To the solution was added 0.1 ml of a 5% aqueous solution of citric acid, followed by dilution with chloroform. The mixture was washed successively with water and a saline solution, and dried over sodium sulfate. After evaporation of the solvent, the residue was subjected to silica gel column chromatography (chloroform/methanol=9/1) to give 8 mg of Derivative IIa-39.

$^1$H-NMR (DMSO-d$_6$) δ(ppm): 1.086(3H, t, J=7.1 Hz), 1.099 (3H, t, J=7.1 Hz), 1.948(1H, dd, J=4.8, 14.1 Hz), 2.107(3H, s), 3.158(4H, m), 3.910(3H, s), 4.880(1H, d, J=17.7 Hz), 4.931(1H, d, J=16.9 Hz), 7.028(1H, dd, J=5.0, 7.1 Hz), 7.332–8.287(5H, m), 8.838(1H, d, J=2.1 Hz)

FAB-MS (m/z): 640 (M+1)$^+$

9) Derivatives IIa-51 and IIa-56

Compound (E$^a$) (Japanese Published Unexamined Patent Application No. 295588/88; supra) (60.7 mg, 0.1 mmol) was dissolved in a mixture of 5 ml of chloroform and 1 ml of methanol, and then 11 mg (0.3 mmol) of sodium borohydride was added thereto under ice cooling, followed by stirring at the same temperature for 15 minutes. After dilution with chloroform, the mixture was washed successively with water and a saline solution, and dried over potassium carbonate. After evaporation of the solvent, the residue was subjected to silica gel column chromatography (Chloroform/methanol/triethylamine=98/2/0.5) to give 36 mg (yield 59%) of Compound (F$^a$).

$^1$H-NMR (DMSO-d$_6$) δ(ppm): 1.650(3H, s), 2.027(1H, dd, J=4.9, 14.5 Hz), 2.126(3H, s), 3.843(1H, dd, J=7.4, 14.5 Hz), 3.891(3H, s), 4.607(2H, s), 4.673(2H, s), 5.125(2H, s), 7.099(1H, dd, J=5.0, 7.3 Hz), 7.437–7.907(5H, m), 8.812(1H, d, J=0.8 Hz)

FAB-MS (m/z): 612 (M+1)$^+$

Compound (F$^a$) (159 mg, 0.26 mmol) was dissolved in 15 ml of chloroform, and then 0.8 ml (10.4 mmol) of ethanethiol and 24 mg (0.104 mmol) of camphorsulfonic acid were added thereto, followed by stirring at room temperature for 12 hours. The solution was washed successively with a saturated aqueous solution of sodium bicarbonate, water, and a saline solution, and dried over sodium sulfate. After evaporation of the solvent, the residue was subjected to silica gel column chromatography (ethyl acetate/toluene=1/9—chloroform/methanol=99/1) to give 43 mg of Compound (G$^a$) and 75 mg of Compound (H$^a$).

Compound (G$^a$)

$^1$H-NMR (CDCl$_3$) δ(ppm): 1.292(3H, t, J=7.4 Hz), 1.297 (3H, t, J=7.4 Hz), 1.799(3H, s), 2.141(1H, dd, J=5.0, 14.5 Hz), 2.256(3H, s), 2.532(2H, q, J=7.4 Hz), 2.553(2H, q, J=7.4 Hz), 2.869(3H, s), 3.971(1H, dd, J=7.5, 14.5 Hz), 3.992(3H, s), 4.005 (3H, s), 4.021(2H, s), 5.416(1H, dd, J=17.5 Hz), 5.459(1H, d, J=17.4 Hz), 6.989(1H, dd, J=5.1, 7.4 Hz), 7.509–7.963(5H, m), 9.134 (1H, d, J=1.2 Hz)

FAB-MS (m/z): 700 (M+1)$^+$

Compound (H$^a$)

$_1$H-NMR (CDCl$_3$) δ(ppm): 1.294(3H, t, J=7.4 Hz), 1.799(3H, s), 2.149(1H, dd, J=5.0, 14.6 Hz), 2.273(3H, s), 2.533(2H, q, J=7.4 Hz), 2.813 (3H, s), 3.972(1H, dd, J=7.4, 14.6 Hz), 4.008(3H, s), 4.015(2H, s), 4.951 (2H, s), 5.377(1H, d, J=17.4 Hz), 5.418(1H, d, J=17.4 Hz), 6.973(1H, dd, J=5.0, 7.5 Hz), 7.481–8.037 (5H, m), 9.093(1H, d, J=1.2 Hz)

FAB-MS (m/z): 656 (M+1)$^+$

Substantially the same procedure as performed for the synthesis of Derivative IIa-39 was repeated using 34 mg of Compound (G$^a$) to give 18.7 mg of Derivative IIa-51.

$^1$H-NMR (CDCl$_3$) δ(ppm): 1.300(3H, t, J=7.4 Hz), 1.325(3H, t, J=7.4 Hz), 2.185(3H, s), 2.514(1H, dd, J=4.8, 14.5 Hz), 2.540(2H, q, J=7.4 Hz), 2.555(2H, q, J=7.4 Hz), 3.384(1H, dd, J=7.5, 14.5 Hz), 3.941(2H, s), 3.976(2H, s), 4.094(3H, s), 4.836(1H, d, J=16.4 Hz), 4.910(1H, d, J=16.3 Hz), 5.781 (1H, s), 6.845 (1H, dd, J=4.8, 7.5 Hz), 7.371–7.843(5H, m), 8.998(1H, s)

FAB-MS (m/z): 616 (M+1)$^+$

Substantially the same procedure as performed for the synthesis of Derivative IIa-39 was repeated using 30 mg of Compound (H$^a$) to give 20.4 mg of Derivative IIa-56.

$^1$H-NMR (CDCl$_3$) δ(ppm): 1.280(3H, t, J=7.4 Hz), 2.144(3H, s), 2.391(1H, dd, J=4.9, 14.5 Hz), 2.517(2H, q, J=7.4 Hz), 3.320(1H, dd, J=7.4, 14.5 Hz), 3.885(2H, s), 4.069(3H, s), 4.521(1H, d, J=16.3 Hz), 4.631(1H, d, J=16.7 Hz), 4.804(2H, s), 5.769(1H, s), 6.830(1H, dd, J=4.8, 7.4 Hz), 7.375–7.771(5H, m), 8.934(1H, s)

FAB-MS (m/z): 572 (M+1)$^+$

The reaction of compounds C$^a$ through H$^a$ is summarized in FIG. 1.

10) Derivative IVa-2

Compound III wherein X is CO$_2$CH$_3$, R$^1$ is Br, and R$^2$ is H; (see Japanese Published Unexamined Patent Application No. 120388/87; hereby incorporated by reference) (50 mg, 0.09 mmol) was dissolved in a mixture of 0.5 ml of trifluoroacetic acid and 50 μl of 3N HCl, and the solution was stirred at room temperature for 2 days. The precipitates were collected by filtration and subjected to high performance liquid chromatography (Unisil $_5$C$_{18}$; methanol/water=8/2) to give 8.4 mg of Derivative IVa-2.

$^1$H-NMR (DMSO-d$_6$) δ(ppm): 4.947 (2H, s), 7.300–8.010 (6H, m), 8.249(1H, s), 9.266(1H, d, J=2.0 Hz)

FAB-MS (m/z): 390 (M+1)$^+$

Figure 2:
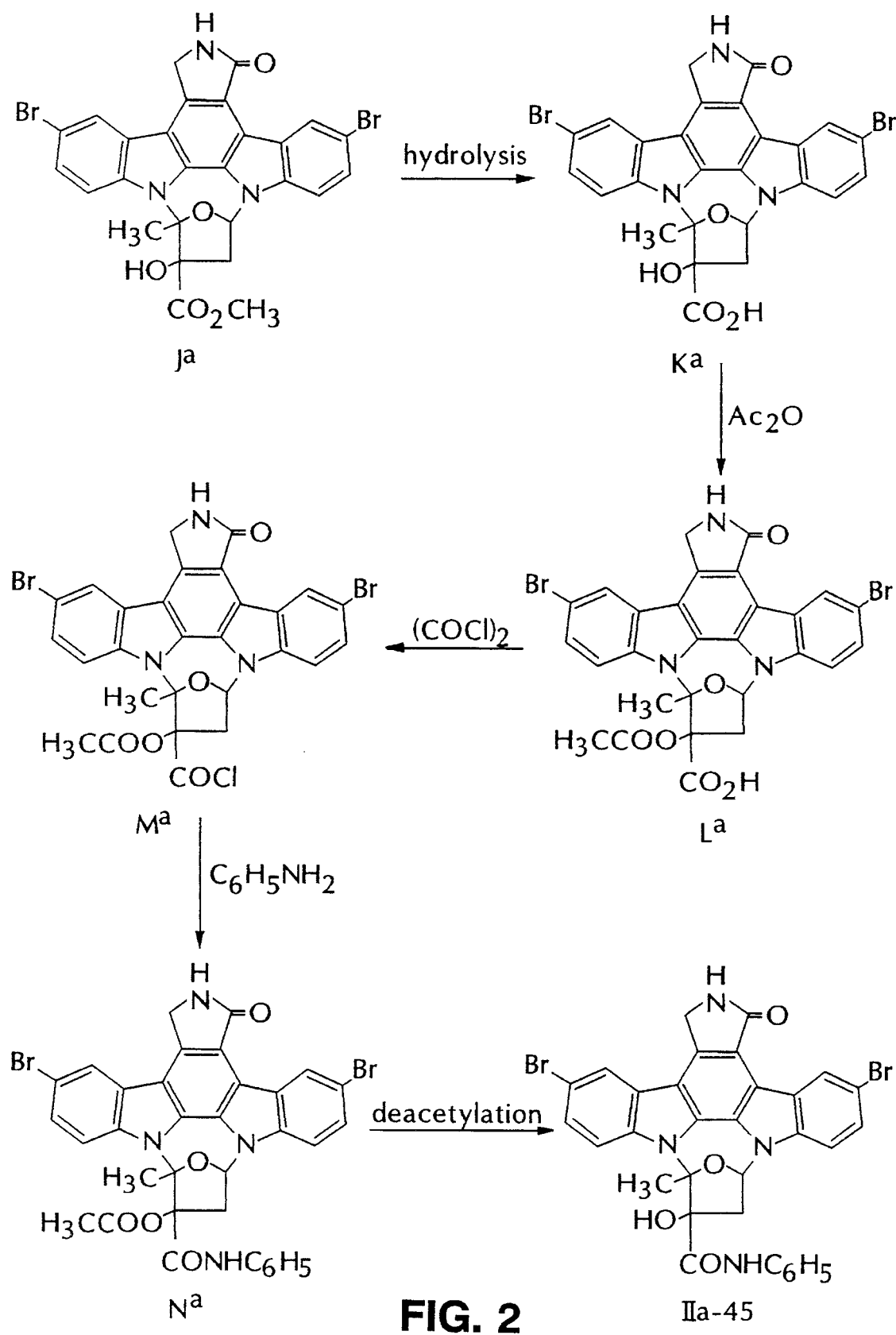
FIG. 2 is a drawing outlining the chemical synthesis of indolocarbazoles $K^a$, $M^a$, $L^a$, $N^a$, and IIa-45.

Derivative IIa-45 can be prepared by the reaction steps shown in FIG. 2.

11) Derivative IIa-45

Compound (J$^a$) (200 mg) was dissolved in 1 ml of dimethylformamide, and then 0.25 ml of an aqueous solution of 23.5 mg of sodium hydroxide was added thereto, followed by stirring at room temperature of 4 hours. After 1N hydrochloric acid was added to adjust the pH of the solution to 1–2, the precipitates were collected by filtration to give 178 mg (yield 91%) of Compound (K$^a$).

$^1$H-NMR (DMSO-d$_6$) δ(ppm): 1.965(1H, dd, J=4.8, 14.0 Hz), 2.184(3H, s), 3.364(1H, dd, J=7.5, 14.0 Hz), 5.029 (1H, d, J=18.1 Hz), 5.071(1H, d, J=18.0 Hz), 7.133 (1H, dd, J=4.9, 7.5 Hz), 7.595–8.189(5H, m), 8.733 (1H, s), 9.398(1H, d, J=2.1 Hz)

Compound (K$^a$) (168 mg), was dissolved in 3 ml of pyridine, and then 0.44 ml (4.7 mmol) of acetic anhydride was added thereto, followed by stirring at room temperature for 4 days. After evaporation of the solvent, 4 ml of 1N hydrochloric acid was added to the residue, and the precipitates were collected by filtration to give 182 mg (yield quantitative) of Compound (L$^a$).

$^1$H-NMR (DMSO-d$_6$) δ(ppm): 1.684 (3H, s), 2.135(1H, dd, J=4.9, 14.4 Hz), 2.252(3H, s), 3.865(1H, dd, J=7.6, 14.5 Hz), 5.063(2H, s), 7.255(1H, dd, J=4.9, 7.5 Hz), 7.612–8.582(5H, m), 8.760(1H, s), 9.389(1H, d, J=2.1 Hz)

Compound (L$^a$) (172 mg) was suspended in thionyl chloride, followed by stirring at 90° C for 4.5 hours. After evaporation of the solvent, diethyl ether was added to the residue and the precipitates were collected by filtration to give 180 mg of Compound ($M^a$).

Compound ($M^a$) (67 mg, 0.1 mmol) was dissolved in 2 ml of ethylene dichloride, and then 180 μl of aniline in tetrahydrofuran was added thereto under ice cooling, followed by stirring at the same temperature for 1 hour. After evaporation of the solvent, the residue was dissolved in a mixture of 2 ml of tetrahydrofuran and 0.5 ml of methanol, and then 1 ml of 1N NaOH was added thereto, followed by stirring at room temperature for 3 hours. To the solution was added 1N hydrochloric acid (1.2 ml) for neutralization, followed by dilution with tetrahydrofuran. The mixture was washed with a saline solution and dried over sodium sulfate. After evaporation of the solvent, the residue was subjected to silica gel column chromatography (chloroform/methanol=98/2) to give Compound IIa-45 (13 mg from 56 mg of isolated Compound $N^a$).

$^1$H-NMR (DMSO-$d_6$) δ(ppm): 2.110 (1H, dd, J=4.9, 13.9 Hz), 2.175(3H, s), 5.019(1H, d, J=18.1 Hz), 5.088(1H, d, J=18.0 Hz), 6.887(1H, s), 7.119–8.201(11H, m), 8.711 (1H, s), 9.391(1H, d, J=2.2 Hz), 10.071(1H, s)

FAB-MS (m/z): 687 (M+1)$^+$

The reaction of Compounds $J^a$ through $N^a$ and Derivative IIa-45 are summarized in FIG. 2.

Other preferred indolocarbazoles can be represented by formulae I, II, III, IV, and V as shown below:

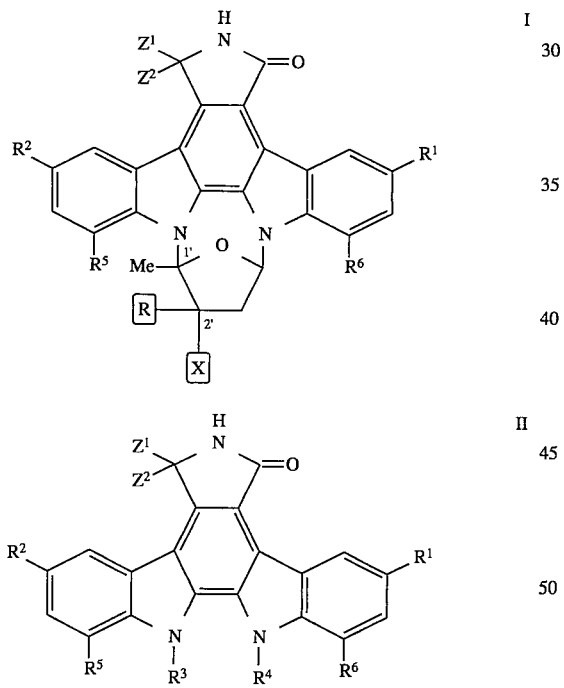
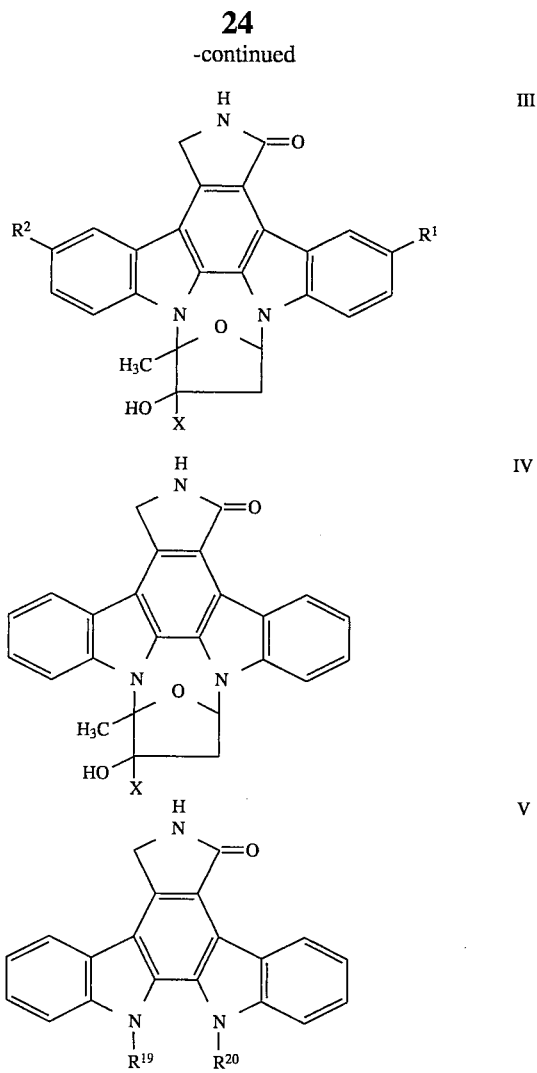

wherein the following substitutions are made in Table 5, below.

TABLE 5

| Derivative[1] | X | R | R$^1$ | Z$^1$, Z$^{2[2]}$ |
|---|---|---|---|---|
| I-1 | CO$_2$CH$_3$ | OH | H | H, H |
| I-2 | CH$_2$OH | OH | H | H, H |
| I-3 | H | OH | H | H, H |
| I-4 | CONH$_2$ | OH | H | H, H |
| I-5 | CO$_2$CH$_3$ | OH | OH | H, H |
| I-6 | CH$_2$OCOCH$_3$ | OH | H | H, H |
| I-7[3] | —CH$_2$NHCO$_2$— | — | H | H, H |
| I-8 | CH$_2$SOCH$_3$ | OH | H | H, H |
| I-9 | CONHC$_2$H$_5$ | OH | H | H, H |

TABLE 5-continued

| Derivative[1] | X | R | R[1] | $Z^1, Z^{2[2]}$ |
|---|---|---|---|---|
| I-10 | $CONHC_3H_7$ | OH | H | H, H |
| I-11 | CON O | OH | H | H, H |
| I-12 | $CONH(CH_2)_2OH$ | OH | H | H, H |
| I-13[3] | $-CH_2OC(CH_3)_2O-$ | — | H | H, H |
| I-14 | $CH=NNHCONH_2$ | OH | H | H, H |
| I-15[3] | $-CH_2N(CH_3)CO_2-$ | — | H | H, H |
| I-16 | $CH_2N(CH_3)_2$ | OH | H | H, H |
| I-17[4,12] | $CH_2NH$-Pro | OH | H | H, H |
| I-18[4] | $CH_2NH$-Ser | OH | H | H, H |
| I-19 | $CH_2OH$ | $OCH_3$ | H | H, H, |
| I-20[5] | $CH_2S$-Glc | OH | H | H, H |
| I-21 | $CH_2N_3$ | OH | H | H, H |
| I-22 | $CO_2CH_3$ | OH | H | O |
| I-23 | $CO_2CH_3$ | OH | Br | H, H |
| I-24 | $CH_2NHCOCH_3$ | OH | H | H, H |
| I-25 | $CON(CH_3)_2$ | OH | H | H, H |
| I-26 | CONHOH | OH | H | H, H |
| I-27 | $CO_2CH_3$ | OH | $NHCONHC_6H_5$ | H, H |
| I-28 | CH=NOH | OH | H | H, H |
| I-29 | $CH=NNHC(=NH)-NH_2$ | OH | H | H, H |
| I-30 | $CH=NNH-$ | OH | H | H, H |
| I-31 | $CH_2CO_2CH_3$ | OH | H | H, H |
| I-32[4,12] | $CH_2NH$-Gly | OH | H | H, H |
| I-33 | $CONHC_6H_5$ | OH | H | H, H |
| I-34 | $CO_2CH_3$ | OH | $NHCONHC_2H_5$ | H, H |
| I-35 | $CO_2CH_3$ | OH | $CH_2OCONHC_2H_5$ | H, H |
| I-36 | $CH_2OH$ | OH | Br | H, H |
| I-37 | $CO_2CH_3$ | OH | $NHCO_2CH_3$ | H, H |
| I-38 | $CO_2CH_3$ | OH | $CH_3$ | H, H |
| I-39[6] | $CO_2CH_3$ | OH | Br | H, H |
| I-40 | $CH_2SO-$ | OH | H | H, H |
| I-41 | $CO_2CH_3$ | OH | $CH_2OC_2H_5$ | H, H |
| I-42[6] | $CH_2OH$ | OH | Br | H, H |
| I-43[6] | $CONHCH_2CH_2OH$ | OH | Br | H, H |
| I-44[7] | $CO_2CH_3$ | OH | Cl | H, H |
| I-45 | $CONH_2$ | OH | Br | H, H |
| I-46 | $CH_2NHCONHC_2H_5$ | OH | H | H, H |
| I-47 | $CH_2NHCONHC_6H_5$ | OH | H | H, H |
| I-48 | $CH=NN(C_6H_5)_2$ | OH | H | H, H |
| I-49 | $CH_2SC_6H_5$ | OH | H | H, H |
| I-50 | $CH_2S$-(pyridyl) | OH | H | H, H |
| I-51 | $CH_2SOC_6H_5$ | OH | H | H, H |
| II-1[8] | — | — | H | H, H |
| II-2[9,11] | — | — | H | H, H |
| II-3[10,11] | — | — | H | H, H |

[1]$R^2$ is hydrogen except where noted in footnotes 6, 7, and 8. $R^5$ and $R^6$ are hydrogen.
[2]$Z^1$ and $Z^2$ are both hydrogen, or both are combined together to represent oxygen, where indicated.
[3]X and R are combined together to form the linking group.
[4]NH— amino acid linkage is an amide bond through the carboxyl group of the amino acid.
[5]Glc is glucose; linkage is through the 1-position.
[6]$R^2$ is Br.
[7]$R^2$ is Cl.
[8]$R^3$ and $R^4$ are $CH_2CH=CH_2$.
[9]$R^3$ is $CH_2CH=CH_2$; $R^4$ is H.
[10]$R^3$ is H; $R^4$ is $CH_2CH=CH_2$.
[11]A 1.5 to 1.0 mixture of components II-2 and II-3.
[12]Compound is in the form of the hydrochloride.

12) Derivative III-1

Derivative III-1 (Compound III in which $R^1$ and $R^2$ are each independently halogen, and X is $CH_2OH$) can be prepared by the following reaction step:

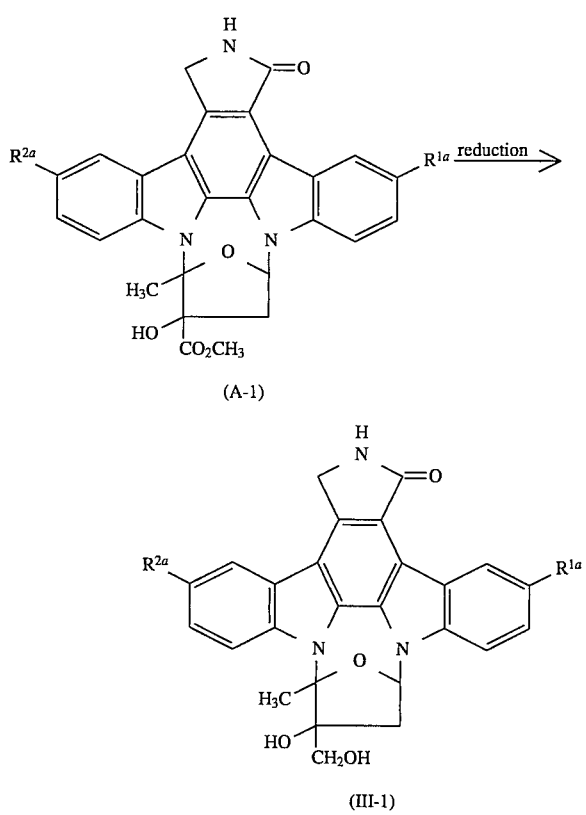

$R^{1a}$ and $R^{2a}$ independently represent halogen.

The starting compound (A-1) is disclosed in Japanese Published Unexamined Patent Application No. 120388/87.

Derivative (III-1) can be obtained by treatment of Compound (A-1) with 2 to 10 equivalents of a reducing agent in an inert solvent. An example of the reducing agent is sodium borohydride. An example of the inert solvent is a mixed solvent of an ether such as diethyl ether or tetrahydrofuran and an alcohol such as methanol or ethanol. The ratio of the ether to the alcohol is preferably 1:1 to 5:1. The reaction is completed in 3 to 24 hours at 0° to 50° C.

13) Derivative III-2

Figure 3:
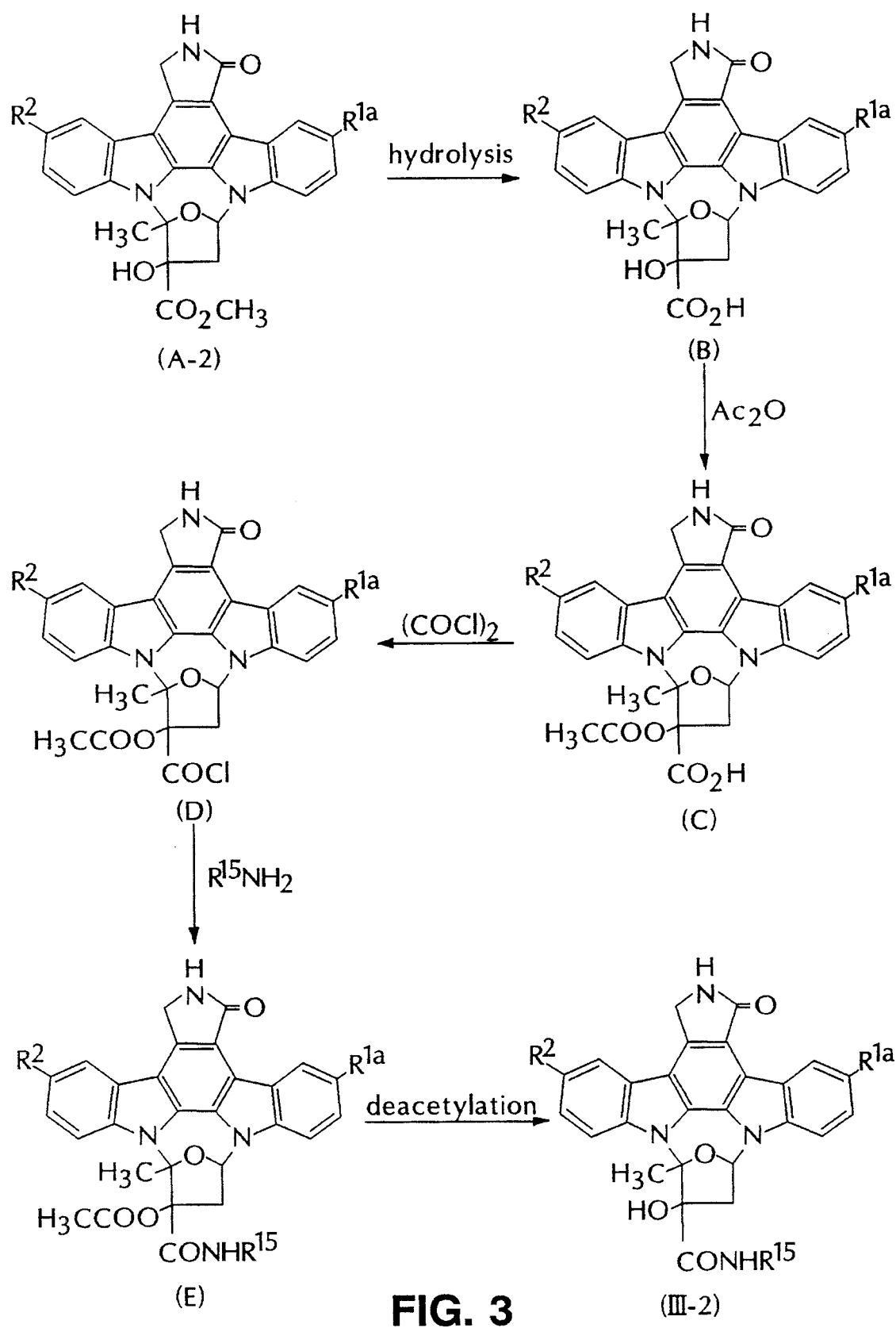
FIG. 3 is a drawing outlining the chemical synthesis of indolocarbazoles B, D, C, E, and III-2.

Derivative III-2 (Compound III, in which $R^1$ is halogen, $R^2$ is hydrogen or halogen, and X is $CONHR^{15}$) can be prepared by the following reaction steps, which are illustrated in FIG. 3. In the formulae, $R^{1a}$, $R^2$, are either a hydrogen or a halogen and $R^{15}$ is hydrogen, hydroxy lower alkyl or aryl.

The starting compound (A-2) is disclosed in Japanese Published Unexamined Patent Application No. 120388/87 (supra).

Compound (B) can be obtained by hydrolysis of Compound (A-2) with 1 to 1.5 equivalents of an alkali metal hydroxide. Examples of the alkali metal hydroxide are sodium hydroxide and potassium hydroxide. As a reaction solvent, dimethylformamide or the like is used. The reaction is completed in 1 to 24 hours at 0° to 50° C.

Compound (C) can be obtained by reaction of Compound (B) with 3 to 20 equivalents of an acetylating agent. An example of the acetylating agent is acetic anhydride. As a reaction solvent, pyridine or the like is used. The reaction is completed in 1 hours to 4 days at 0° to 50° C.

Compound (D) can be obtained by reaction of Compound (C) with a halogenating agent of a carboxyl group, which serves also as a solvent. Examples of the halogenating agent are thionyl chloride and oxalyl chloride. The reaction is completed in 1 to 3 hours at 50° to 100° C.

Compound (E) can be obtained by reaction of Compound (D) with 5 to 30 equivalents of $R^{15}NH_2$. As a reaction solvent, a halogenated hydrocarbon such as methylene chloride, chloroform, or ethylene dichloride, dimethylformamide, or the like is used. The reaction is completed in 1 to 24 hours at 0° to 50° C.

Compound (III-2) can be obtained by deacetylation of Compound (E) with 0.5 to 10 equivalents of a deacetylating agent. Examples of the deacetylating agent are alkali metal alkoxylate such as sodium methylate and alkali metal hydroxide such as sodium hydroxide. As a reaction solvent, a mixed solvent of a halogenated hydrocarbon such as methylene chloride, chloroform, or ethylene dichloride and an alcohol such as methanol or ethanol, a mixed solvent of an ether such as dioxane or tetrahydrofuran and an alcohol such as methanol or ethanol, or the like is used. The ratio of the halogenated hydrocarbon to the alcohol, or that of the ether to the alcohol is 1:5 to 1:1. The reaction is completed in 5 minutes to 1 hour at 0° to 50° C.

14) Derivative III-3

Figure 4:
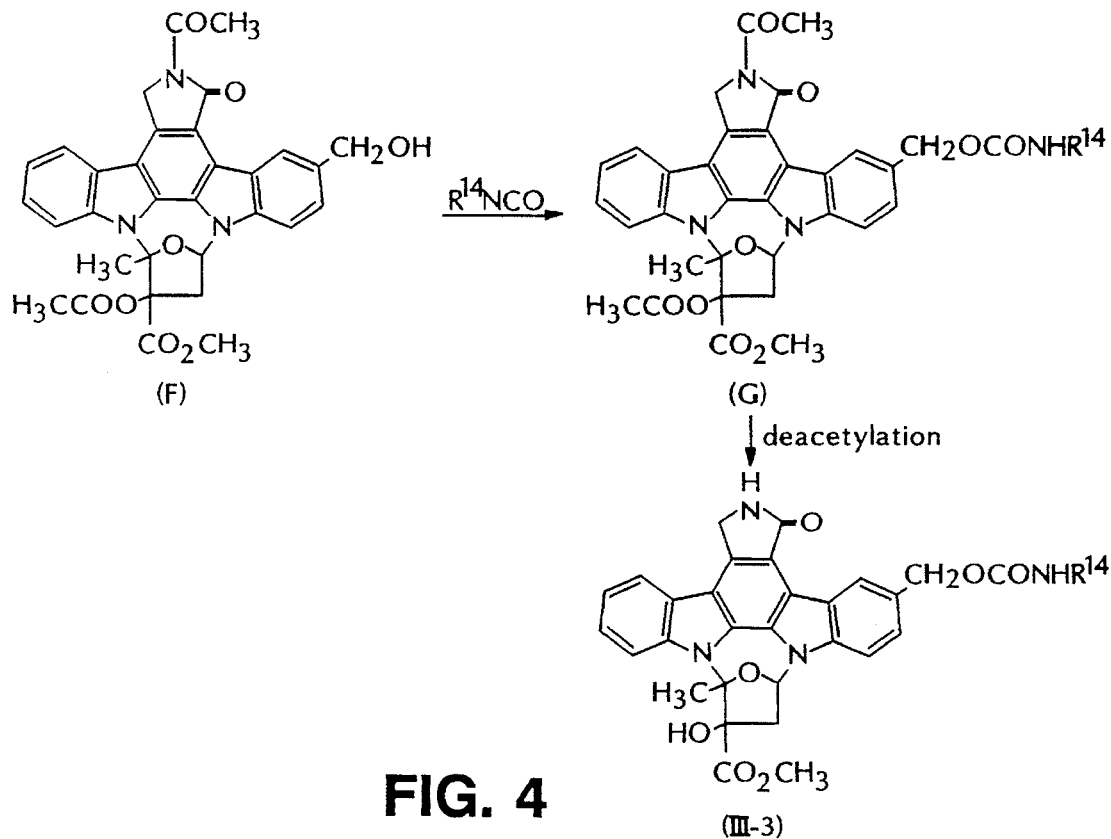
FIG. 4 is a drawing outlining the chemical synthesis of indolocarbazoles G and III-3.

Derivative III-3 (Compound III in which $R^1$ is $CH_2OCONHR^{14}$ and X is $CO_2CH_3$) can be prepared by the following reaction steps, which are illustrated in FIG. 4. (In the formulae, $R^{14}$ represents lower alkyl.)

The starting compound (F) is disclosed in Japanese Published Unexamined Patent Application No. 295588/88 (hereby incorporated by reference).

Compound (G) can be obtained by reaction of Compound (F) with 1 to 5 equivalents of $R^{14}NCO$ in the presence of a base. An example of the base is triethylamine. As a reaction solvent, a mixed solvent of tetrahydrofuran and dimethylformamide, or the like is used. The ratio of tetrahydrofuran to dimethylformamide is 5:1 to 1:1. The reaction is completed in 5 to 24 hours at 10° to 70° C.

Compound (III-3) can be obtained from Compound (G) in a manner similar to that of the preparation of Compound (III-2).

15) Derivative III-4

Figure 5:
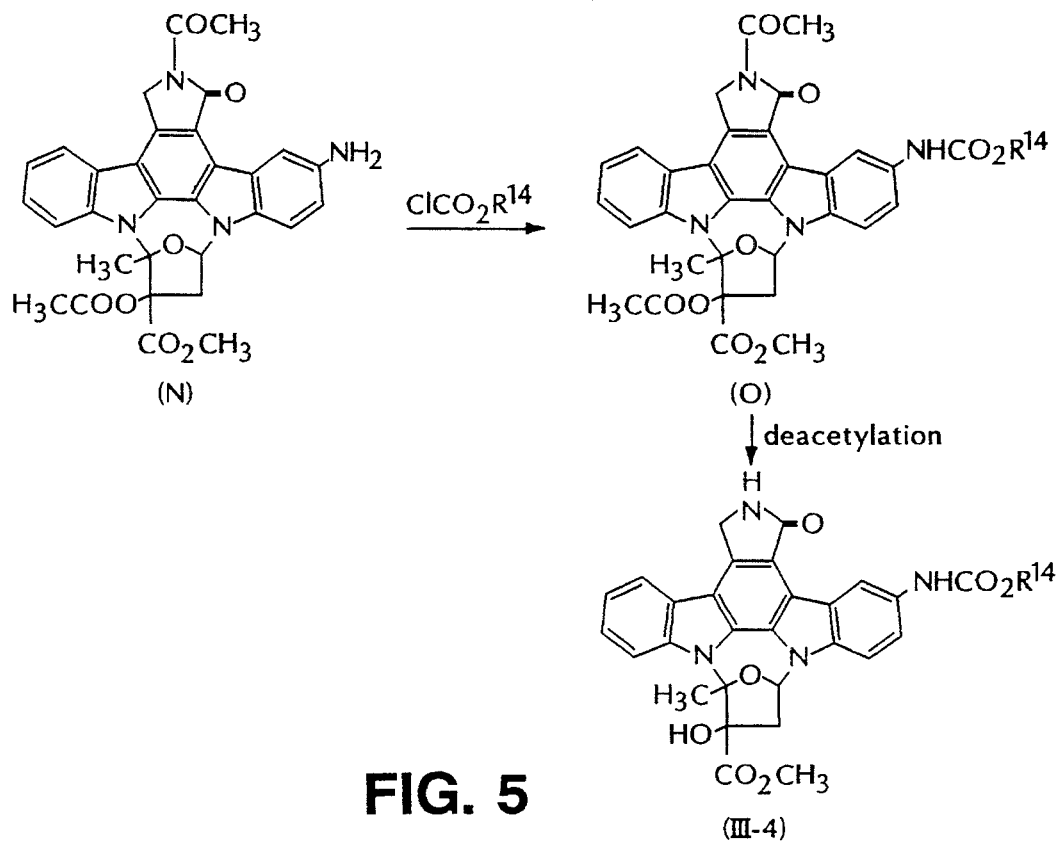
FIG. 5 is a drawing outlining the chemical synthesis of indolocarbazoles O and III-4.

Derivative III-4 (Compound III in which $R^1$ is $NHCO_2R^{14}$ and X is $CO_2CH_3$) can be prepared by the following reaction steps depicted in FIG. 5. (In the formulae, $R^{14}$ represents lower alkyl).

The starting compound (N) is disclosed in Japanese Published Unexamined Patent Application No. 295588/88 (hereby incorporated by reference).

Compound (O) can be obtained by reaction of Compound (N) with 1 to 5 equivalents of $ClCO_2R^{14}$ in the presence of 1 to 5 equivalents of a base. An example of the base is triethylamine. As a reaction solvent, a halogenated hydrocarbon such as methylene chloride, chloroform, or ethylene dichloride, or the like is used. The reaction is completed in 1 to 3 hours at 0° to 50° C.

Derivative (III-4) can be obtained from Compound (O) in a manner similar to that in the preparation of Compound (III-2).

16) Derivative IV-1

Derivative IV-1 (Compound IV in which X is $CH_2SR^{16}$) can be prepared by the following reaction step:

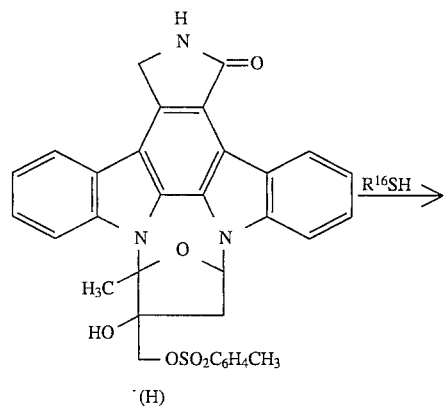
(H)

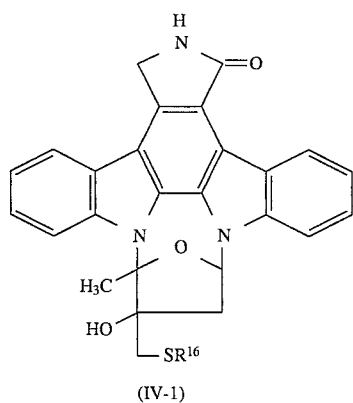
(IV-1)

(In the formulae, $R^{16}$ is aryl, or a heterocyclic group including a nitrogen atom.

The starting compound (H) is disclosed in Japanese Published Unexamined Patent Application No. 155285/87 (hereby incorporated by reference).

Derivative IV-1 can be obtained by reaction of Compound (H) with 1 to 5 equivalents of $R^{16}SH$ in the presence of 1 to 5 equivalents of a base. An example of the base is alkali metal hydride such as sodium hydride. As a reaction solvent, dimethylformamide or the like is used. The reaction is completed in 2 to 5 hours at 0° to 50° C.

17) Derivative IV-2

Derivative IV-2 (Compound IV in which X is $CH_2S(O)R^{16}$) can be prepared by the following reaction step:

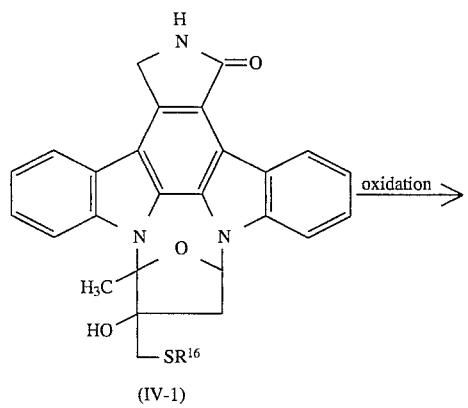
(IV-1)

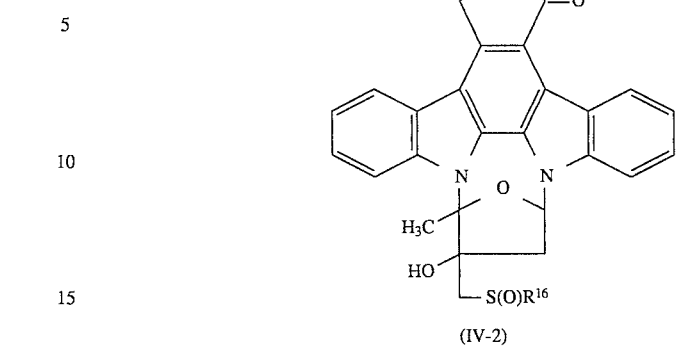
(IV-2)

Derivative IV-2 can be obtained by treatment of Compound (IV-1) with 1 to 1.5 equivalents of an oxidant. An example of the oxidant is m-chloroperbenzoic acid. As a reaction solvent, a halogenated hydrocarbon such as methylene chloride, chloroform, or ethylene dichloride, or the like is used. The reaction is completed in 1 to 8 hours at $-70°$ to 0° C.

18) Derivative IV-3

Derivative IV-3 (Compound IV in which X is $CH_2NHCONHR^{18}$) can be prepared by the following reaction step:

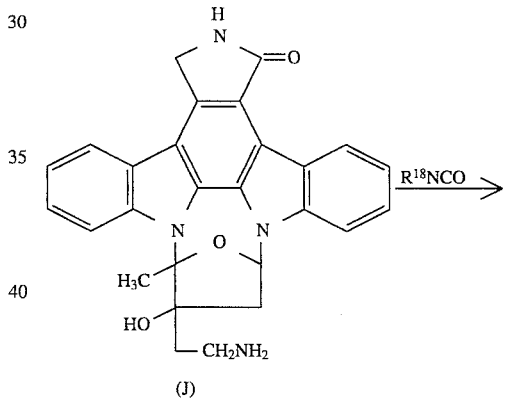
(J)

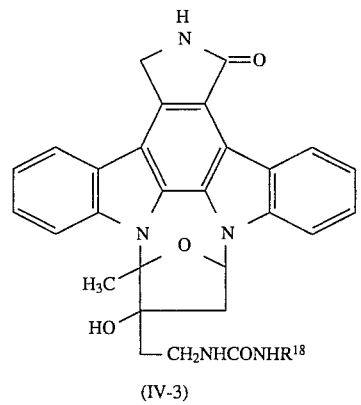
(IV-3)

(In the formulae, $R^{18}$ represents lower alkyl or aryl.)

The starting compound (J) is disclosed in Japanese Published Unexamined Patent Application No. 155285/87 (hereby incorporated by reference).

Derivative IV-3 can be obtained by reaction of Compound (J) with 1 to 3 equivalents of $R^{18}NCO$ in the presence of 1 to 3 equivalents of a base. An example of the base is triethylamine. As a reaction solvent, tetrahydrofuran or the like is used. The reaction is completed in 1 to 5 hours at 0° to 50° C.

Derivative IV-4

Derivative IV-4 (Compound IV in which X is CH=NN($R^{17}$)$_2$) can be prepared by the following reaction step:

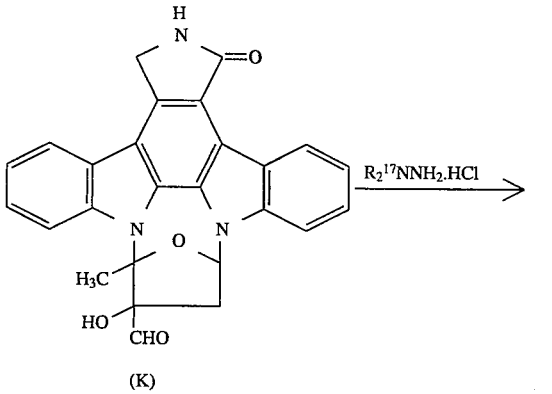

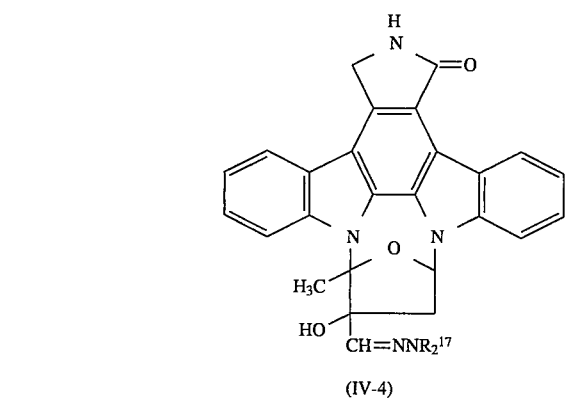

(IV-4)

(In the formulae, $R^{17}$ represents aryl.)

The starting compound (K) is disclosed in Japanese Published Unexamined Patent Application No. 295588/88 (supra).

Compound (IV-4) can be obtained by reaction of Compound (K) with 2 to 10 equivalents of $R^{17}_2NNH_2.HCl$. As a reaction solvent, a mixed solvent of an ether such as dioxane or tetrahydrofuran and water, or the like is used. The ratio of the ether to water is 1:10 to 1:2. The reaction is completed in 2 to 8 hours at 0° to 50° C.

20) Derivative IV-5

Figure 6:
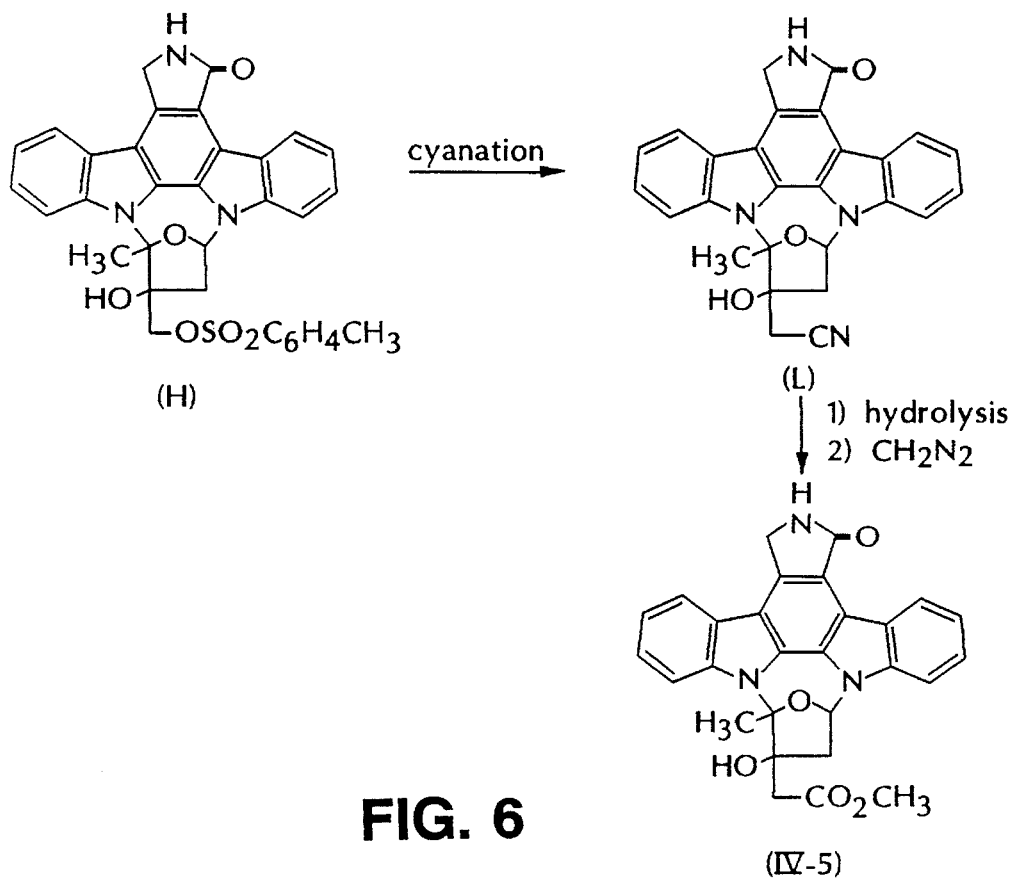
FIG. 6 is a drawing outlining the chemical synthesis of indolocarbazoles L and IV-5.

Derivative IV-5 (Compound IV in which X is $CH_2CO_2CH_3$) can be prepared by the following reaction steps, which are illustrated in FIG. 6.

Compound (L) can be obtained by reaction of Compound (H) with 1 to 5 equivalents of a cyanating agent. An example of the cyanating agent is an alkali metal cyanide such as sodium cyanide. As a reaction solvent, dimethylformamide or the like is used. The reaction is completed in 1 to 24 hours at 20° to 100° C.

Derivative IV-5 can be obtained by hydrolysis of Compound (L) with 10 to 50 ml/mmol of an aqueous solution of an alkali metal hydroxide, followed by treatment with 2 to 10 equivalents of $CH_2N_2$. Examples of the aqueous solution of an alkali metal hydroxide are a 30% aqueous solution of sodium hydroxide and a 30% aqueous solution of potassium hydroxide. In the hydrolysis, ethylene glycol or the like is used as a reaction solvent, and the reaction is completed in 1 to 3 hours at 120° to 180° C. In the treatment with $CH_2N_2$, dimethylformamide or the like is used as a reaction solvent, and the reaction is completed in 1 to 5 hours at 0° to 30° C.

21) Derivative V

Figure 7:
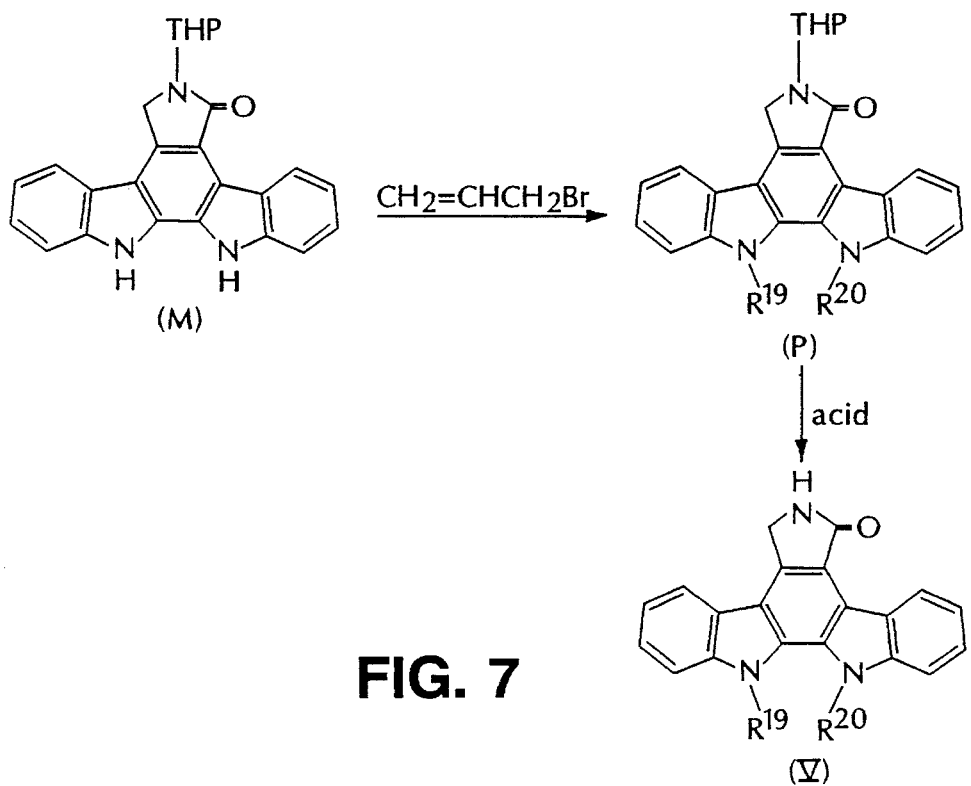
FIG. 7 is a drawing outlining the chemical synthesis of indolocarbazoles P and V.

Derivative V can be prepared by the following reaction steps, which are illustrated in FIG. 7. (In the formulae, THP represents tetrahydropyranyl; one of $R^{19}$ and $R^{20}$ is hydrogen and the other is allyl, or both of them are allyl.)

The starting compound (M) is disclosed in J. Chem. Soc. Perkin Trans. I, 2475 (1990).

Compound (P) can be obtained by reaction of Compound (M) with 1 to 1.5 equivalents of allyl bromide in the presence of 1 to 1.5 equivalents of a base. An example of the base is an alkali metal hydride such as sodium hydride. As a reaction solvent, dimethylformamide or the like is used. The reaction is completed in 1 to 5 hours at −10° to 10° C.

Derivative V can be obtained by treatment of Compound (P) with 4 to 50 ml/mmol of an aqueous solution of an acid. An example of the aqueous solution of an acid is 2M $H_2SO_4$. As a reaction solvent, tetrahydrofuran or the like is used. The reaction is completed in 5 to 24 hours at 50° to 100° C.

22) Derivative I-45

Compound A-2 (FIG. 3; $R^{1a}$=Br, $R^2$=H) (250 mg, 0.46 mmol) was dissolved in 1 ml of dimethylformamide, and then 0.25 ml of an aqueous solution of 23.5 mg of sodium hydroxide was added thereto, followed by stirring at room temperature for 4 hours. After 1N hydrochloric acid was added to adjust the pH of the solution to 1–2, the precipitates were collected by filtration to give 223 mg (yield 91%) of Compound B-1 ($R^{1a}$=Br, $R^2$=H).

$^1$H-NMR (DMSO-$d_6$) δ(ppm): 2.00(1H, dd, J=5.1, 14.0 Hz), 2.22(3H, s), 5.01(2H, s), 7.10(1H, dd, J-5.7, 7.0 Hz), 7.26–8.08(6H, m), 8.65(1H, s), 9.36(1H, d, J-2 Hz)

Compound B-1 (FIG. 3; $R^{1a}$=Br, $R^2$=H) (210 mg, 0.39 mmol) was dissolved in 3 ml of pyridine, and then 0.44 ml (4.7 mmol) of acetic anhydride was added thereto, followed by stirring at room temperature for 4 days. After evaporation of the solvent, 4 ml of 1N hydrochloric acid was added to the residue, and the precipitates were collected by filtration to give 223 mg (yield 99%) of Compound C-1 ($R^{1a}$=Br, $R^2$=H).

$^1$H-NMR (DMSO-$d_6$) δ(ppm): 1.66 (3H, s), 2.48 (3H, s), 5.02(2H, s), 7.16–8.08(7H, m), 8.69(1H, s), 9.34 (1H, d, J=2 Hz)

Compound C-1 (FIG. 3; $R^{1a}$=Br, $R^2$=H) (100 mg, 0.17 mmol) was suspended in 3 ml of thionyl chloride, followed by stirring at 90° C for 4.5 hours. After evaporation of the solvent, diethyl ether was added to the residue, and the precipitates were collected by filtration to give 84 mg (yield 83%) of Compound D-1 ($R^{1a}$=Br, $R^2$=H).

Compound D-1 (FIG. 3; $R^{1a}$=Br, $R^2$=H) (84 mg, 0.39 mmol) was dissolved in 2 ml of ethylene dichloride, and then 3 ml of 0.8% $NH_3$/tetrahydrofuran was added thereto under ice cooling, followed by stirring at the same temperature for 1 hour. After evaporation of the solvent, the residue was dissolved in a mixture of 2 ml of tetrahydrofuran and 0.5 ml of methanol, and then 1 ml of 1N NaOH was added thereto, followed by stirring at room temperature for 3 hours. To the solution was added 1N hydrochloric acid (1.2 ml) for neutralization, followed by dilution with tetrahydrofuran. The mixture was washed with a saline solution and dried over sodium sulfate. After evaporation of the solvent, the residue was subjected to silica gel column chromatography (chloroform/methanol=98/2) to give 54 mg (yield 72%) of Derivative I-45.

$^1$H-NMR (DMSO-$d_6$) δ(ppm): 2.018 (1H, dd, J=4.6, 13.7 Hz), 2.183(3H, s), 4.985(1H, d, J=17.0 Hz), 5.054(1H, d, J=17.1 Hz), 6.308(1H, s), 7.057(1H, dd, J=4.9, 7.5 Hz), 7.353–8.092(8H, m), 8.696(1H, s), 9.385(1H, d, J=2.1 Hz)
SIMS (m/z): 531 (M+1)$^+$ 23) Derivative I-35

Compound F (FIG. 4) (70 mg, 0.12 mmol) was dissolved in a mixture of 3 ml of tetrahydrofuran and 1 ml of dimethylformamide, and then 34 μl (0.24 mmol) of triethylamine and 19 μl (0.24 mmol) of ethyl isocyanate were added thereto, followed by stirring at 50° C for 6 hours. After dilution with chloroform, the mixture was washed successively with water and a saline solution, and dried over sodium sulfate. After evaporation of the solvent, the residue was subjected to silica gel column chromatography (chloroform/methanol=99/1) to give 71 mg (yield 91%) of Compound (G-1, $R^{14}$=$C_2H_5$).

$^1$H-NMR (CDCl$_3$) δ(ppm): 1.16(3H, t, J-7.3 Hz), 1.800(3H, s), 2.150(1H, dd, J-5.1, 14.5 Hz), 2.282(3H, s), 2.849(3H, s), 3.273(1H, m), 3.978(1H, dd, J=7.5, 14.5 Hz), 4.011(3H, s), 5.355(2H, brs), 5.406(1H, d, J=17.4 Hz), 5.449(1H, d, J=17.4 Hz), 7.007(1H, dd, J=5.1, 7.4 Hz), 7.427–8.098(6H, m), 9.245(1H, s)

FAB-MS (m/z ): 652 (M)$^+$

Compound (G-1, $R^{14}$=$C_2H_5$) (44 mg, 0.067 mmol) was dissolved in a mixture of 1 ml of ethylene dichloride and 0.5 ml of methanol, and then 13 μl of 28% sodium methoxide/methanol was added thereto, followed by stirring at room temperature for 20 minutes. Amberlist 15 was added to the mixture for neutralization and insoluble matters were filtered off. After evaporation of the solvent, the residue was subjected to preparative TLC (chloroform/methanol=95/5) to give 68.9 mg (yield 24%) of Derivative I-35.

$^1$H-NMR (CDCl$_3$) δ(ppm): 1.103(3H, t, J=7.2 Hz), 2.163(3H, s), 2.282(1H, dd, J=5.0, 14.3 Hz), 3.184(2H, q, J=7.2 Hz), 3.288(1H, dd, J=7.5, 14.3 Hz), 4.023(3H, s), 4.866(1H, d, J=17.0 Hz), 4.937 (1H, d, J=16.9 Hz), 5.230(2H, s), 6.856(1H, dd, J=5.0, 7.5 Hz), 7.306–7.882(6H, m), 9.148 (1H, s)

FAB-MS (m/z) :569 (M+1)$^+$

24) Derivative I-37

Compound (N; FIG. 5) (98 mg, 0.17 mmol) was dissolved in 5 ml of ethylene dichloride, and then 39 μl of methyl chloroformate and 71 μl of triethylamine were added thereto, followed by stirring at room temperature for 1.5 hours. Methanol (1 ml) was added to the solution and the solvent was evaporated. The residue was subjected to preparative TLC (chloroform/methanol=98/2) and the crude product obtained was recrystallized from ethyl acetate to give 18 mg (yield 17%) of Compound (0-1; $R^{14}$=$CH_3$).

$^1$H-NMR (CDCl$_3$) δ(ppm):1.783(3H, s), 2.125(1H, dd, J=5.0, 14.6 Hz), 2.269(3H, s), 2.810(3H, s), 3.828 (3H, s), 3.965(1H, dd, J-7.4, 14.6 Hz), 4.007(3H, s), 5.357(1H, d, J=17.8 Hz), 5.403(1H, d, J=17.6 Hz), 6.963(1H, dd, J=4.9, 7.6 Hz), 7.411–8.071(6H, m), 8.944(1H, d, J=2.0 Hz)

Substantially the same procedure as in the preparation of I-35 was repeated using 8 mg (0.013 mmol) of Compound (0-1; $R^{14}$=$CH_3$) obtained above to give 5 mg (yield of Derivative I-37.

$^1$H-NMR (DMSO-d$_6$) δ(ppm): 1.999 ( 1H, dd, J=4.6, 13.9 Hz), 2.146(3H,s), 3.373(1H, dd, J=7.7, 14.2 Hz), 3.688 (3H, s), 3.924(3H, s), 4.959(1H, d, J=17.6 Hz), 5.020(1H, d, J=17.6 Hz), 6.311(1H, s), 7.081(1H, dd, J=5.0, 7.0 Hz), 7.333–8.052(6H, m), 8.553(1H, s)

FAB-MS (m/z ): 541 (M+1)$^+$

25) Derivative I-42

Compound A-1-1, in which $R^{1a}$ and $R^{2a}$=Br (Derivative III-1 preparation) (62.5 mg, 0.1 mmol) was dissolved in a mixture of 3 ml of tetrahydrofuran and 1 ml of methanol, and then 19 mg (0.5 mmol) of sodium borohydride was added thereto, followed by stirring at room temperature for 12 hours. After being adjusted to pH 1–2 with 1N hydrochloric acid, the mixture was washed with a saline solution and dried over sodium sulfate. After evaporation of the solvent, the residue was subjected to preparative TLC (chloroform/methanol=95/5) to give 37 mg (yield 62%) of Derivative I-42.

$^1$H-NMR (DMSO-d$_6$) δ(ppm): 1.918 (1H, dd, J=4.9, 5.1 Hz), 2.140 (3H, s), 3. 149 (1H, dd, J+7.3, 7.6 Hz), 3.728–3.836(2H, m), 5.009(1H, d, J=17.8 Hz), 5.070(1H, d, J=17.5 Hz), 5.144(1H, t, J=5.1 Hz), 5.439(1H, s), 6.994(1H, dd, J=4.9, 7.5 Hz), 7.573–8.184(5H, m), 8.701(1H, s), 9.387(1H, d, J=2.2 Hz)

FAB-MS (m/z ): 598 (M+1)$^+$

26) Derivative I-43

Substantially the same amidation procedure as in the preparation of 1-45 was repeated using 67 mg (0.1 mmol) of Compound D-2 ($R^{1a}$=$R^2$=Br in FIG. 3) and 120 μl of ethanolamine and then substantially the same deacetylation procedure as in the preparation of Derivative I-35 was repeated to give 30 mg of Derivative I-43.

$^1$H-NMR (DMSO-d$_6$) δ(ppm): 2.009 (1H, dd, J=4.7, 13.9 Hz), 2.102(3H, s), 4.832(1H, t, J=5.5 Hz), 5.004(1H, d, J=17.3 Hz), 5.073(1H, d, J=17.3 Hz), 6.509(1H, s), 7.055(1H, dd, J=4.7, 7.3 Hz), 7.586–8.270(6H, m), 8.695(1H, s), 9.380(1H, d, J=2.2 Hz)

FAB-MS (m/z): 655 (M+1)$^+$

Derivative I-46

Compound (J, in preparation of IV-3) (43.8 mg, 0.1 mmol) was dissolved in 1 ml of tetrahydrofuran, and then 12 μl (0.15 mmol) of ethyl isocyanate and 28 μl (0.2 mmol) of triethylamine were added thereto, followed by stirring at room temperature for 2 hours. After evaporation of the solvent, the residue was subjected to preparative TLC (chloroform/methanol=9/1) to give 11 mg (yield 22%) of Derivative I-46.

$^1$H-NMR (DMSO-d$_6$) δ(ppm): 1.051 (3H, t, J=7.2 Hz), 1.964 (1H, dd, J=5.3, 13.5 Hz), 2.145(3H, s), 2.959(1H, dd, J=7.6, 13.8 Hz), 3.111(2H, m), 4.965(1H, d, J=17.4 Hz), 5.031(1H, d, J=17.6 Hz), 5.835(1H, s), 6.138(1H, t, J=5.7 Hz), 6.265(1H, t, J=5.4 Hz), 6.925 (1H, dd, J=5.4, 7.4 Hz), 7.253–8.059(7H, m), 8.584 (1H, s), 9.200(1H, d, J=7.8 Hz)

FAB-MS (m/z): 510 (M+1)$^+$

28) Derivative I-47

Substantially the same procedure as in the preparation of 1-46 was repeated using 43.8 mg (0.1 mmol) of Compound (J) and 13 μl of phenyl isocyanate to give 13 mg (yield 23%) of Derivative I-47.

$^1$H-NMR (DMSO-d$_6$) δ(ppm): 2.063(1H, dd, J=5.2, 13.4 Hz), 2.180(3H, s), 2.999(1H, dd, J=7.3, 13.6 Hz), 3.635–3.727(2H, m), 4.965(1H, d, J=17.1 Hz), 5.043(1H, d, J=17.4 Hz), 5.776(1H, s), 6.445(1H, dd, J=4.6, 6.6 Hz), 6.928(1H, t, J=7.4 Hz), 7.007(1H, dd, J=5.5, 7.3 Hz), 7.243–8.074(11H, m), 8.583(1H, s), 8.830 (1H, s), 9.198(1H, d, J=7.8 Hz)

FAB-MS (m/z): 558 (M+1)$^+$

29) Derivative I-48

Compound (K, preparation of Derivative IV-4) (44 mg, 0.1 mmol) was dissolved in a mixture of 3 ml of tetrahydrofuran and 0.3 ml of water, and then 110 mg (0.5 mmol) of 1,1-diphenylhydrazine-hydrochloride was added thereto, followed by stirring at room temperature for 4 hours. After dilution with chloroform, the mixture was washed successively with a 10% aqueous solution of hydrogen chloride, water, and a saline solution, and dried over sodium sulfate. After evaporation of the solvent, the residue was subjected to preparative TLC (chloroform/methanol=97/3) to give 30 mg of Compound 1-48.

¹H-NMR (DMSO-d$_6$) δ(ppm): 2.012 (3H, s), 2.137 (1H, dd, J=5.2, 13.5 Hz), 3.588(1H, dd, J=7.4, 13.2 Hz), 4.973 (1H, d, J=17.3 Hz), 5.031(1H, d, J=17.3 Hz), 6.086 (1H, s), 6.885(1H, s), 7.105(1H, dd, J=5.4, 7.3 Hz), 7.250–8.045(17H, m), 8.590(1H, s), 9.230(1H, d, J=7.8 Hz)

FAB-MS (m/z): 604 (M+1)$^+$

30) Derivative I-49

Compound (H, preparation of Derivative IV-i) (59.3 mg, 0.1 mmol) was dissolved in 1 ml of dimethylformamide, and then 21 μl of thiophenol and 8 mg (0.2 mmol) of sodium hydride (60%) were added thereto, followed by stirring at room temperature for 3.5 hours. After dilution with chloroform, the mixture was washed successively with a saturated aqueous solution of sodium bicarbonate, water, and a saline solution, and dried over sodium sulfate. After evaporation of the solvent, the residue was subjected to silica gel column chromatography (chloroform/methanol=99/1) to give 22 mg (yield 41%) of Derivative I-49.

¹H-NMR (CDCl$_3$) δ(ppm): 2.211(3H, s), 2.661(1H, dd, J=5.7, 14.4 Hz), 3.423(1H, dd, J=7.6, 14.5 Hz), 3.537 (1H, d, J=13.0 Hz), 3.734(1H, d, J=13.0 Hz), 4.545 (1H, d, J=17.3 Hz), 4.761(1H, d, J=17.3 Hz), 6.568 (1H, dd, J=5.5, 7.4 Hz), 7.091–8.003(12H, m), 8.736 (1H, d, J=7.9 Hz)

FAB-MS (m/z): 532 (M+1)$^+$

31) Derivative I-50

Substantially the same procedure as in the preparation of I-49 was repeated using 59.3 mg of Compound (H) and 22.2 mg of 2-mercaptopyridine to give 38.7 mg (yield 73%) of Derivative I-50.

¹H-NMR (CDCl$_3$) δ(ppm): 2.326(3H, s), 2.401(1H, m), 3.339(1H, dd, J=7.4, 14.5 Hz), 3.571(1H, d, J=14.9 Hz), 4.130(1H, d, J=14.8 Hz), 4.918(1H, d, J=16.6 Hz), 5.002(1H, d, J=16.7 Hz), 6.723(1H, dd, J=6.0, 7.4 Hz), 7.173–8.468(11H, m), 9.177 (1H, d, J=7.7 Hz)

FAB-MS (m/z): 533 (M+1)$^1$

31a) Derivative I-51

Derivative I-49 (15 mg, 0.028 mmol) was dissolved in 0.38 ml of chloroform, and then 0.2ml of chloroform containing 4.8 mg of m-chloroperbenzoic acid was added thereto at −48° C followed by stirring at the same temperature for 2 hours. After dilution with chloroform, the mixture was washed successively with a saturated aqueous solution of sodium bicarbonate and a saline solution, and dried over sodium sulfate. After evaporation of the solvent, the residue was recrystallized from chloroform to give 6.1 mg (yield 40%) of Derivative I-51.

¹H-NMR (DMSO-d$_6$) δ(ppm): 2.100 (0.87H, s), 2.189(2.13H, s), 4.982(1H, d, J=18.0 Hz), 5.038(1H, d, J=17.9 Hz), 6.056(0.71H, s), 6.337(0.29H, s), 7.145–8.073(12H, m), 8.583(1H, s), 9.200(0.29H, d, J=7.4 Hz), 9.207 (0.71H, d, J=8.3 Hz)

FAB-MS (m/z): 548 (M+1)$^+$

32) Derivative I-40

Substantially the same procedure as in the preparation of I-51 was repeated using 30 mg of Compound I-50 and 9.5 mg of m-chloroperbenzoic acid to give 12.8 mg (yield 42%) of Derivative I-40.

¹H-NMR (DMSO-d$_6$) δ(ppm): 2.134(0.25H, s), 2.185(0.75H, s), 4.981(1H, d, J=7.9 Hz), 5.040(1H, d, J=7.6 Hz), 6.212(0.75H, s), 6.449(0.25H, s), 7.088–8.228(11H, m), 8.598(1H, s), 8.809(0.25H, m), 8.919(0.75H, m), 9.198(0.25H, d, J=7.2 Hz), 9.213(0.75H, d, J=7.7 Hz)

FAB-MS (m/z): 549 (M+1)$^+$

33) Derivatives II-1, II-2, and II-3

Compound (M; FIG. 7) (337 mg, 0.85 mmol) was dissolved in 10 ml of dimethylformamide, and 41 mg (1.02 mmol) of sodium hydride (60%) was added thereto under ice cooling, followed by stirring at the same temperature for 10 minutes. Allyl bromide (88 μl, 1.02 mmol) was added thereto and the solution was stirred for 1 hour under ice cooling. To the solution was added 1 ml of methanol, followed by dilution with chloroform. The mixture was washed successively with water and a saline solution, and dried over sodium sulfate. After evaporation of the solvent, the residue was subjected to silica gel column chromatography (ethyl acetate/toluene=1/9) to give 217 mg (yield 54%) of Compound (P-1; $R^{19}$=$R^{20}$=allyl) and 109 mg (yield 30%) of a mixture of Compound (P-2; $R^{19}$=H, $R^{20}$=allyl) and Compound (P-3; $R^{19}$=allyl, $R^{20}$=H) (1/1.4).

Compound (P-1; $R^{19}$=$R^{20}$=allyl)

¹H-NMR (DMSO-d$_6$) δ(ppm): 5.044–5.478(11H, m), 6.084–6.223(2H, m), 7.295–8.176(7H, m), 9.415(1H, d, J=7.8 Hz)

FAB-MS (m/z): 476 (M+1)$^+$

A mixture of Compound (P-2; $R^{19}$=H, $R^{20}$=allyl) and Compound (P-3; $R^{19}$=allyl, $R^{20}$=H) (1/1.4)

¹H-NMR (DMSO-d$_6$) δ(ppm): 4.694 (0.58H, dd, J=1.3, 17.3 Hz), 4.757(0.42H, d, J=17.0 Hz), 5.003–5.172 (3H, m), 4.465(1H, dd, J=1.7, 10.9 Hz), 5.565–5.619 (2H, m), 6.111–6.222(1H, m), 7.135– 8.177(7H, m), 9.302(0.42H, d, J=8.1 Hz), 9.353(0.58H, d, J=8.1 Hz), 11.555(0.42H, s), 11.713(0.58H, s)

FAB-MS (m/z): 436 (M+1)$^+$

Compound P-1 (in which $R^{19}$=$R^{20}$=allyl in FIG. 7) (205 mg, 0.43 mmol) was dissolved in 20 ml of tetrahydrofuran, and 16 ml of a 2M aqueous solution of sulfuric acid was added thereto, followed by stirring at 70° C for 8 hours. After dilution with ethyl acetate, the mixture was washed successively with water and a saline solution, and dried over sodium sulfate. After evaporation of the solvent, the residue was recrystallized from chloroform/ethyl acetate to give 112 mg (yield 66%) of Derivative II-1.

¹H-NMR (DMSO-d$^6$) δ(ppm): 4.965(2H, s), 5.067–5.371 (8H, m), 6.080–6.211 (2H, m), 7.276–8.051(7H, m), 8.571 (1H, s), 9.434(1H, d, J=7.8 Hz)

FAB-MS (m/z): 392 (M+1)$^+$.

Substantially the same procedure as described above was repeated using 100 mg (0.23 mmol) of a mixture of Compound P-2 ($R^{19}$=H, $R^{20}$=allyl) and Compound P-3 ($R^{19}$=allyl, $R^{20}$=H) (1/1.4) to give 39 mg (yield 50%) of a mixture of Derivative II-3 and Derivative II-2 (1.5/1).

¹H-NMR (DMSO-d$_6$) δ(ppm): 4.694 (0.6H, d, J=17.1 Hz), 4.755(0.4H, d, J=17.2 Hz), 4.967(2H, s), 5.008–5.556 (3H, m), 6.145(1H, m), 7.219–8.278(7H, m), 8.463 (1H, s), 9.318 (0.4H, d, J=7.9 Hz), 9.369(0.6H, d, J=7.9 Hz)

FAB-MS (m/Z): 352 (M+1)$^+$.

Other preferred indolocarbazoles can be represented by general formulae Ib, IIb, IIIb, as shown below:

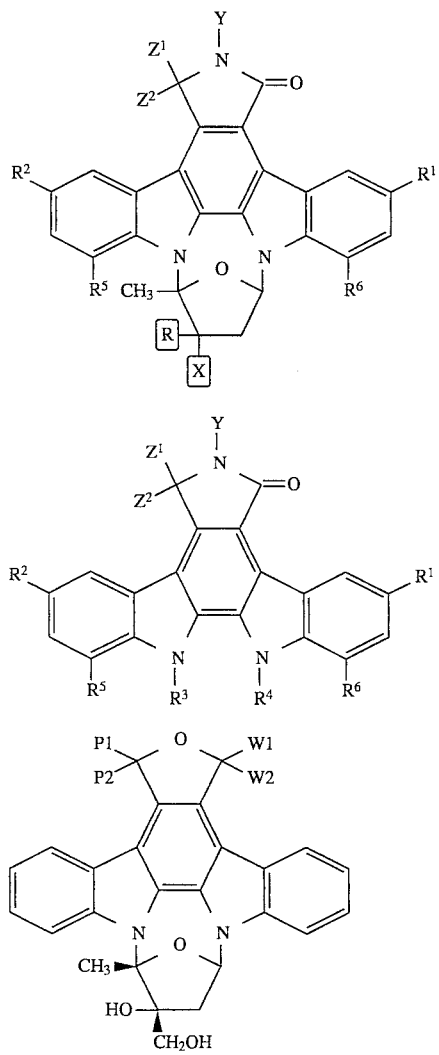

wherein substitutions are shown in Table 6 below:

TABLE 6

| Derivative[1] | Y | X | R | $Z^1Z^{2(2)}$ |
|---|---|---|---|---|
| IIb-1 | CHO | — | — | H,H |
| IIb-2 | H | — | — | O |
| Ib-1 | H | $CO_2CH_3$ | OH | O |
| Ib-2 | H | $CO_2n$-$C_3H_7$ | OH | O |
| Ib-3 | H | $CO_2n$-$C_4H_9$ | OH | O |
| Ib-4 | H | $CO_2n$-$C_6H_{13}$ | OH | O |
| Ib-5 | $CH_3$ | $CO_2CH_3$ | $OCH_3$ | O |
| Ib-6[3] | H | $CO_2CH_3$ | OH | O |
| IIIb-1[7] | — | $CH_2OH$ | OH | — |
| Ib-7 | H | $CONH(CH_2)_2OH$ | OH | H,H |
| Ib-8[6] | H | —$CH_2OC(CH_3)_2O$— | — | O |
| Ib-9[6] | $NH_2$ | —$CH_2OC(CH_3)_2O$— | — | O |
| Ib-10 | $NH_2$ | $CH_2OH$ | OH | O |
| Ib-11 | H | $CONHCH_3$ | OH | O |
| Ib-12[6] | H | —$CH_2NHCO_2$— | — | O |
| Ib-13[6] | H | —$CH_2N(CH_3)CO_2$— | — | O |
| Ib-14 | $CH_3$ | $CH_2OH$ | OH | O |
| Ib-15 | $CH_2CH_2OH$ | $CH_2OH$ | OH | O |
| IIb-3[4] | $CH_3$ | — | — | O |
| IIb-4[5] | $CH_3$ | — | — | O |
| Ib-16 | $NH_2$ | $CH_2NH_2$·HCl | OH | O |
| IIb-5 | $CH_3$ | — | — | O |
| Ib-17 | OH | $CH_2OH$ | OH | O |
| Ib-18 | H | $CO_2CH_3$ | OH | H,OH |
| Ib-19 | H | $CO_2CH_3$ | OH | H, $SC_2H_5$ |
| Ib-20 | H | $CH_2OH$ | OH | H,OH |
| Ib-21[6] | H | —$CH_2N(C_2H_5)CO_2$— | — | O |
| IIIb-2[8] | — | $CH_2OH$ | OH | — |

[1]$R^1$ and $R^2$ are H except as noted in [3]; $R^5$ and $R^6$ are H; $R^3$ and $R^4$ are H except as noted in [4] and [5].
[2]$Z^1$ and $Z^2$ are as noted, or both are combined together to represent oxygen, where indicated.
[3]$R^1$ and $R^2$ are both Br.
[4]$R^3$ is $CH_2CH(OH)CH_2OH$ and $R^4$ is H.
[5]$R^3$ and $R^4$ are both $CH_2CH(OH)CH_2OH$.
[6]X and R are combined together to form the linking group.
[7]P1, P2 are combined together to represent O; W1, W2 = H.
[8]P1, P2 = H; W1, W2 are combined together to represent O.

34) Derivative IIb-1

$POCl_3$ (0.28 ml, 3 mmol) and Compound ($A^b$) (311 mg, 1 mmol) were added to 20 ml of dimethylformamide under ice cooling, followed by stirring at 90° C for 4 hours. The precipitates were collected by filtration, and washed successively with water and methanol to give 250 mg (yield 74% of Derivative $II^b$-1.

The starting material compound ($A^b$) has been disclosed in *J. Antibiot.*, 39:1072 (1986).

The following characteristic values may be obtained by nuclear magnetic resonance spectroscopy (NMR) or mass spectroscopy (MS):

$^1$H-NMR (DMSO-$d_6$) δ(ppm): 5.298(2H, s), 7.255–8.073(7H, m), 9.036(1H, d, J=7.7 Hz), 9.300(1H, s), 11.891(1H, s) 12.175(1H, s)

EI-MS (m/z): 339 (M)$^+$

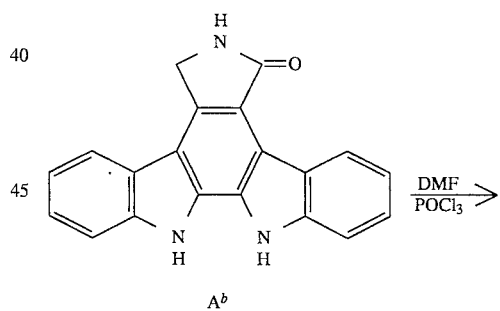

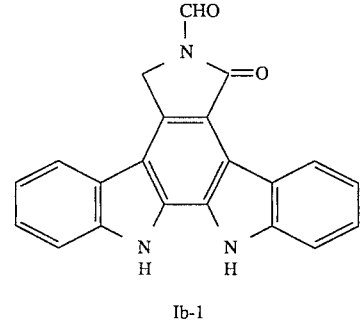

35) Derivative IIb-3

Compound ($B^b$) (208 mg, 0.61 mmol) was dissolved in 20 ml of tetrahydrofuran, and then 74 mg (1.83 mmol) of sodium hydride (60%) was added thereto, followed by stirring at room temperature for 10 minutes. Allyl bromide (0.063 ml, 0.73 mmol) was added thereto and the mixture was stirred at room temperature for 15 hours. To the solution was added a saturated aqueous solution of ammonium chloride, and the organic layer was washed with a saline solution and dried over magnesium sulfate. After evaporation of the solvent, the residue was subjected to silica gel column chromatography (chloroform) to give 135 mg (yield 58%) of Compound ($C^b$).

The following characteristic values for Compound $C^b$ may be obtained by NMR:

$^1$H-NMR (CDCl$_3$+DMSO-d$_6$; 4/1) δ(ppm): 3.04(3H, s), 4.80–5.20(4H, m), 5.96–6.40(1H, m), 7.28–7.72(6H, m), 9.18(1H, d, J=8.0 Hz), 9.20(1H, d, J=8.0 Hz), 9.84(1H, s)

Compound ($C^b$) (145 mg, 0.38 mmol) was dissolved in a mixture of 7 ml of tetrahydrofuran and 0.5 ml of pyridine, and then 4 ml of tetrahydrofuran containing 200 mg of osmium tetroxide was added thereto, followed by stirring at room temperature for 6 hours. Sodium thiosulfate (348 mg), 7 ml of water, and 7 ml of pyridine were added to the reaction solution, followed by stirring at room temperature for 1 hour. To the solution was added tetrahydrofuran for dilution, and the mixture was washed with a saturated aqueous solution of sodium bicarbonate, and dried over magnesium sulfate. After evaporation of the solvent, the residue was subjected to silica gel column chromatography chloroform/methanol=97/3) to give 93 mg of Compound IIb-3.

The starting material Compound ($B^b$) has been disclosed in *Tetrahedron*, 48:8869 (1992).

The following characteristic values may be obtained by NMR and MS:

$^1$H-NMR (DMSO-d$_6$) δ(ppm): 3.186(3H, s), 3.633(2H, m), 4.068(1H, brs), 4.804(1H, dd, J=7.9, 15.6 Hz), 4.955(1H, dd, J=3.2, 15.6 Hz), 5.407(1H, d, J=4.9 Hz), 5.480(1H, t, J=5.1 Hz), 7.351–7.818(6H, m), 9.093 (1H, d, J=7.9 Hz), 9.131(1H, dd, J=0.5, 7.9 Hz), 11.736(1H, s)

FAB-MS (m/z): 414 (M+1)$^+$.

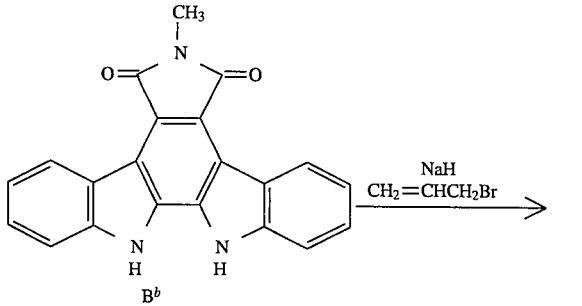

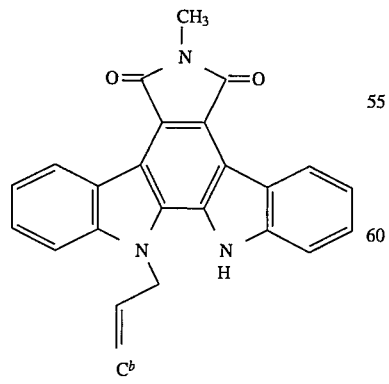

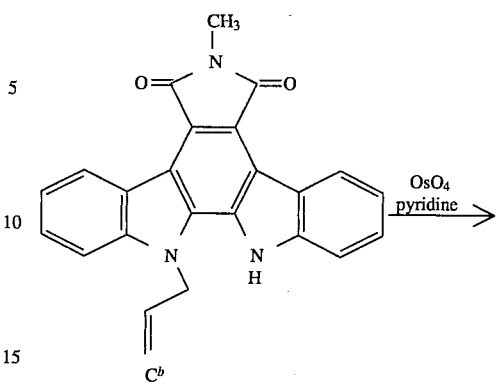

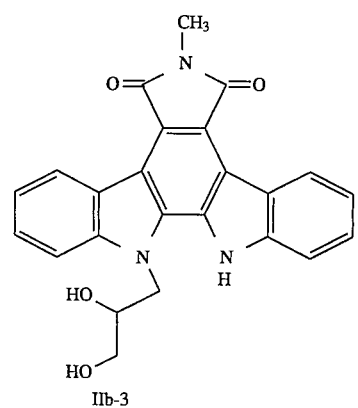

36) Derivative IIb-4

Compound ($D^b$) can be prepared by reaction of Compound ($B^b$) with 2 to 4 equivalents of allyl bromide in the presence of 3 to 5 equivalents of a base. An example of the base is an alkali metal hydride such as sodium hydride. As a reaction solvent, tetrahydrofuran, dimethylformamide, or the like is used. The reaction is completed in 0.5 to 15 hours at −10° to 40° C.

Derivative IIb-4 can be obtained by treatment of Compound ($D^b$) with 2 to 4 equivalents of an oxidant. An example of the oxidant is OsO$_4$. As a reaction solvent, a mixed solvent of tetrahydrofuran and pyridine or the like is used. The ratio of tetrahydrofuran to pyridine is 1/20 to 1/5. The reaction is completed in 3 to 8 hours at 0° to 40° C.

The following characteristic values for Compound ($D^b$) may be obtained by using NMR and MS:

$^1$H-NMR (CDCl$_3$) δ(ppm): 3.21(3H, s), 4.92–6.40(10H, m), 7.40–7.64(6H, m), 9.32(2H, d, J=8.0 Hz)

EI-MS (m/z): 419 (M)$^+$

The following characteristic values for Derivative IIb-4 may be obtained by using NMR and MS:

$^1$H-NMR (DMSO-d$_6$) δ(ppm): 2.965(2H, t, J=5.5 Hz), 3.139(2H, m), 3.196(1.5H, s), 3.198(1.5H, s), 3.626(2H, m), 4.651–4.945(4H, m), 7.399(2H, t, J=7.2 Hz), 7.612 (2H, dt, J=1.2, 7.2 Hz), 7.828(2H, t, J=8.7 Hz), 9.142 (2H, d, J=7.9 Hz)

FAB-MS (m/z): 488 (M+1)⁺

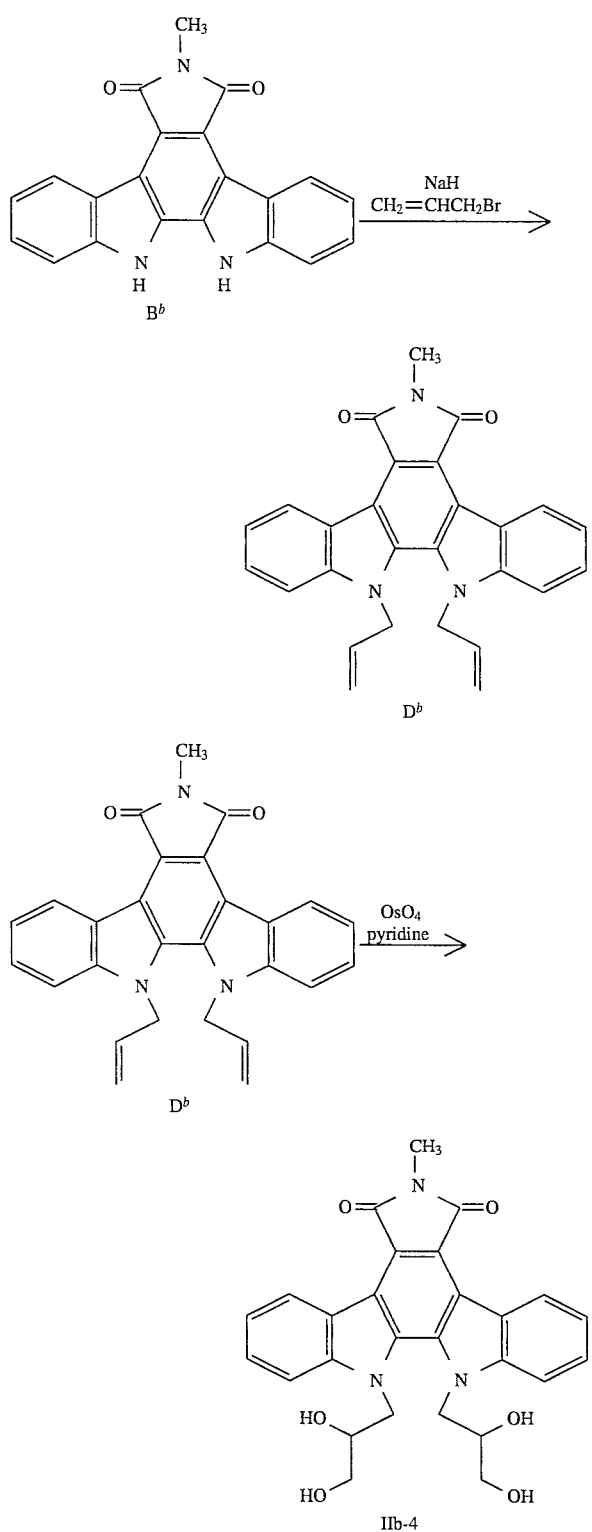

37) Derivatives Ib-9 and Ib-14

Figure 8:
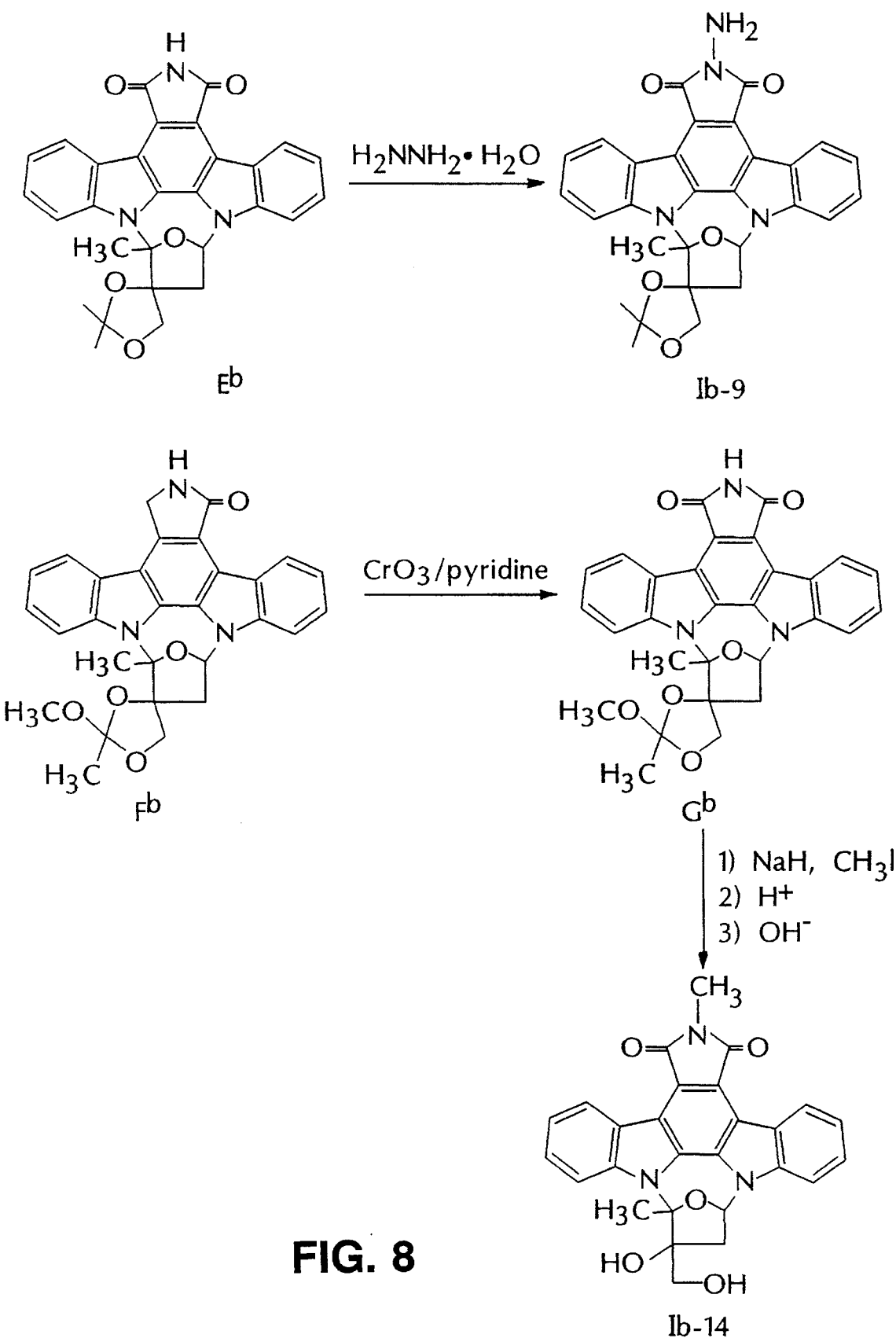
FIG. 8 is a drawing outlining the chemical synthesis of indolocarbazoles Ib-9, $F^b$, $G^b$, and Ib-14.

Compound (E^b) (see FIG. 8 and Japanese Published Unexamined Patent Application No. 295589/88) (49.3 mg, 0.1 mmol) was dissolved in 3 ml of dioxane, and then 0.1 ml of hydrazine hydrate was added thereto, followed by stirring at 110° C for 2 hours. After evaporation of the solvent, methanol was added to the residue and the precipitates were collected by filtration to give 40 mg of Compound Ib-9.

$^1$H-NMR (CDCl$_3$) δ(ppm): 1.19(3H, s), 1.36(3H, s), 2.30 (3H, s), 2.45(1H, dd, J=5.0, 14.0 Hz), 2.91(1H, dd, J=7.0, 14.0 Hz), 4.10(1H, d, J-10 Hz), 4.54(1H, d, J=10 Hz), 6.63(1H, dd, J=5.0, 7.0 Hz), 7.22–7.86(6H, m), 8.97 (1H, d, J=8.0 Hz), 9.25 (1H, d, J=8.0 Hz)

SIMS (m/z): 509 (M+1)⁺

Chromic acid (2.8 g, 28 mmol) was added to 20 ml of pyridine under ice cooling, and then 5 ml of pyridine containing 1.98 g (4 mmol) of Compound (F^b) (see FIG. 8 and Japanese Published Unexamined Patent Application No. 295589/88) was added thereto, followed by stirring at room temperature for 12 hours. After the solution was filtered through Celite, the solvent was evaporated, and the residue was subjected to silica gel column chromatography (chloroform) to give 0.98 g (Yield 48%) of Compound (G^b) see FIG. 8.

The following characteristic values for Compound (G^b) may be obtained by using NMR:

$^1$H-NMR (CDCl$_3$) δ(ppm): 1.52(2.1H, s), 1.60(0.9H, s), 2.32(0.9H, s), 2.36(2.1H, s), 2.67(1H, dd, J=5.0, 14.0 Hz), 3.09(2.1H, s), 3.38(0.9H, s), 4.72–4.81(2H, m), 6.72(1H, m), 7.20–9.32 (8H, m)

Compound (G^b) (305 mg, 0.6 mmol) was dissolved in 6 ml of dimethylformamide, and then 36 mg (0.9 mmol) of sodium hydride (60%) was added thereto under ice cooling, followed by stirring at the same temperature for 10 minutes. Methyl iodide (0.056 ml, 0.9 mmol) was added thereto and the mixture was stirred at the same temperature for 30 minutes. A saturated aqueous solution of ammonium chloride (1 ml) and 10 ml of water were added to the solution and the precipitates were collected by filtration.

The product thus obtained was dissolved in a mixture of 25 ml of chloroform, 1 ml of methanol, and 1 ml of 3N HCl, and the solution was stirred at 60° C for 10 minutes. The solution was washed with a saturated aqueous solution of sodium bicarbonate, and then 10 ml of tetrahydrofuran, 10 ml of methanol, and 1.5 ml of 2N NaOH were added to the organic layer, followed by stirring at room temperature for 10 minutes and evaporation of the solvent. After chloroform was added thereto for dilution, the mixture was washed successively with a 5% aqueous solution of citric acid and a saline solution, and dried over magnesium sulfate. After evaporation of the solvent, the residue was subjected to silica gel column chromatography (chloroform/methanol= 98/2) to give 102 mg (yield 36%) of Derivative Ib-14. The following characteristic values for Derivative Ib-14 may be obtained by using NMR and MS:

$^1$H-NMR (CDCl$_3$+DMSO-d$_6$'41) δ(ppm): 2.24(3H, s), 3.18 (3H, s), 4.81(1H, t, J=6.0 Hz), 6.83(1H, dd, J=5.0, 7.0 Hz), 7.24–8.08(6H, m), 9.06(1H, d, J=7.0 Hz ), 9.25 ( 1H, d, J=7.0 Hz)

EI-MS (m/z): 467 (M+1)⁺

38) Derivatives Ib-15 and Ib-21

Figure 9:
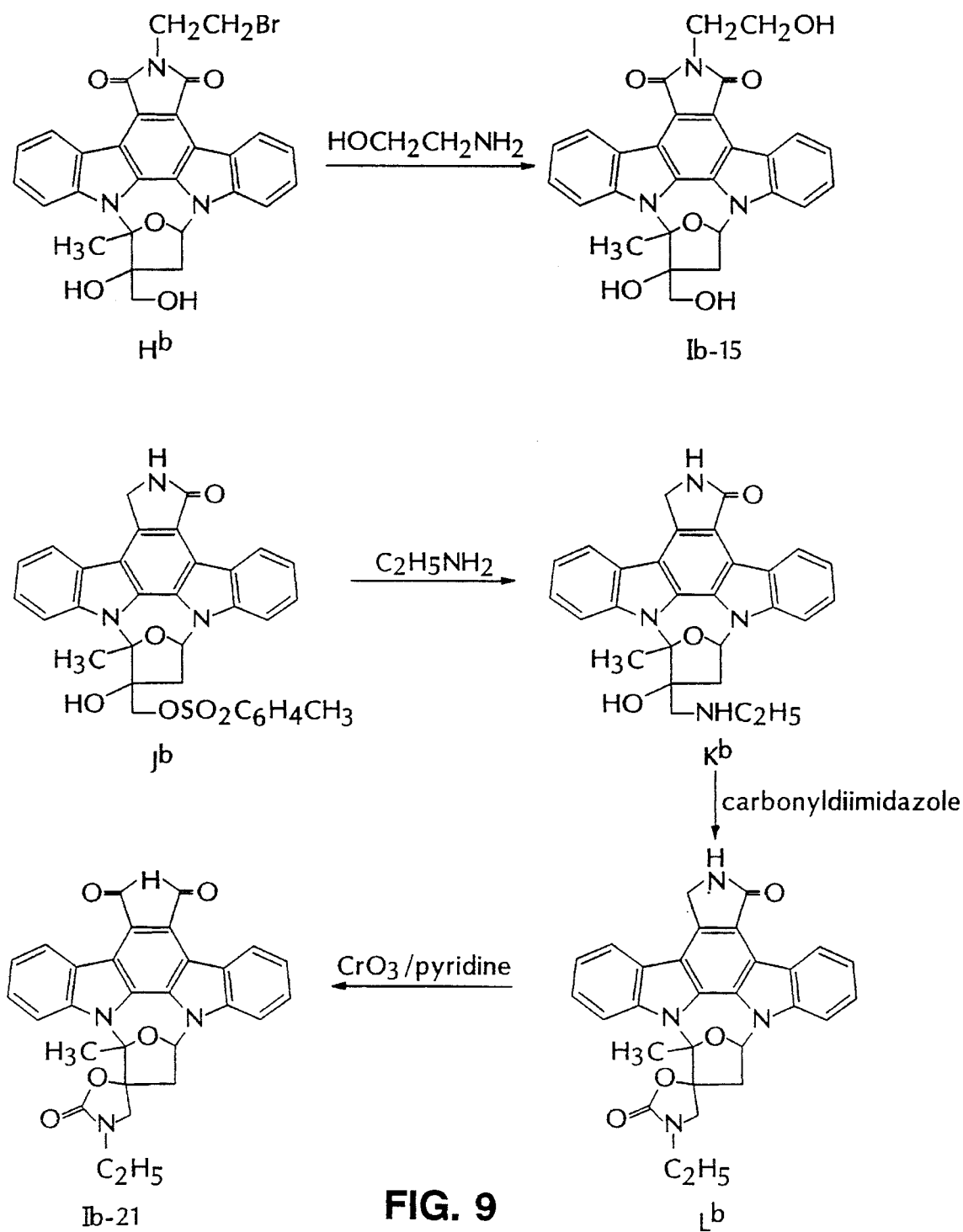
FIG. 9 is a drawing outlining the synthesis of indolocarbazoles Ib-15, $J^b$, $K^b$, $L^b$, and Ib-21.

Compound (H^b) (see FIG. 9 and WO 88/07045) (112 mg, 0.2 mmol) was dissolved in 2 ml of dimethylformamide, and then 195 mg (2 mmol) of ethanolamine hydrochloride and 0.61 ml (4 mmol) of 1,8-diazabicyclo[5,4,0]-7-undecene were added thereto, followed by stirring at room temperature for 3 days. After evaporation of the solvent, the residue was subjected to silica gel column chromatography (chloroform/methanol=98/2) to give 75 mg (yield 25%) of Derivative Ib-15.

The following characteristic values may be obtained by using NMR and MS:

$^1$H-NMR (CDCl$_3$+DMSO-d$_6$; 4/1)δ(ppm): 2.23(3H, s), 4.72 (1H, t, J=5.0 Hz), 4.90(1H, t, J=5.0 Hz), 5.41(1H, s), 6.89(1H, m), 7.32–8.10(6H, m), 9.18(1H, d, J=7.0 Hz), 9.36(1H, d, J=7.0 Hz)

SIMS (m/z): 498 (M+1)+

Compound (J^b) (see FIG. 9 and Japanese Published Unexamined Patent Application No. 155285/87) (890 mg, 1.5 mmol) was dissolved in 10 ml of dimethylformamide, and then 1.43 g (15 mmol) of ethylamine hydrochloride and 2.28 ml (15 mmol) of 1,8-diazabicyclo[5,4,0]-7-undecene were added thereto, followed by stirring at room temperature for 2.5 hours. To the solution was added 10 ml of water and the precipitates were collected by filtration to give 729 mg of Compound (K^b). See FIG. 9.

The following characteristic values may be obtained using NMR:

$^1$H-NMR (DMSO-d$_6$) δ(ppm): 1.32(3H, t), 2.00–2.32(1H, m), 2.16(3H, s), 2.96–3.60(5H, m), 5.00(2H, s), 7.00–7.76(6H, m), 8.02(2H, t, J=8.0 Hz), 8.58(1H, s), 9.18(1H, d, J=8.0 Hz)

Compound (K^b) (650 mg, 1.39 mmol) was dissolved in 7 ml of dimethylformamide, and then 675 mg (4.16 mmol) of carbonyldiimidazole was added thereto, followed by stirring for 3.5 hours. After 10 ml of water was added to the solution, the precipitates were collected by filtration and subjected to silica gel column chromatography (chloroform/methanol=97/3) to given 395 mg (yield 58%) of Compound (L^b). See FIG. 9.

The following characteristic values may be obtained using NMR:

$^1$H-NMR (CDCl$_3$) δ(ppm): 1.30(3H, t, J=7.0 Hz), 2.30(2H, s), 2.68–2.96(2H, m), 3.44(2H, q, J=7.0 Hz), 3.64 (1H, d, J=9.0 Hz), 4.09(1H, d, J=9.0 Hz), 4.97(2H, s), 6.45(1H, brs), 6.76(1H, m), 7.20–8.08(7H, m), 9.32(1H, d, J=8.0 Hz)

Chromic acid (0.49 g, 4.9 mmol) was added to 4 ml of pyridine under ice cooling, and then 2 ml of pyridine containing 345 mg of Compound (L^b) was added thereto, followed by stirring at room temperature for 12 hours. After the solution was filtered through Celite, the solvent was evaporated, and the residue was recrystallized from chloroform/methanol to give 272 mg (yield 77%) of Derivative Ib-21.

The following characteristic values may be obtained by using NMR:

$^1$H-NMR (DMSO-d$_6$) δ(ppm): 1.22(3H, t, J=7.0 Hz), 2.28–2.80(1H, m), 2.36(3H, s), 3.12–3.60(3H, m), 3.86 (1H, brd, J=10.0 Hz), 4.22(1H, brd, J=10.0 Hz), 7.16–8.00(6H, m), 9.04(1H, d, J=8.0 Hz), 9.23(1H, d, J=8.0 Hz)

39) Derivatives IIIb-1 and IIIb-2 are disclosed in Japanese Patent Application No. 4-45782, published as Japanese Kokai 5-247056.

What is claimed is:

1. A solution comprising:
   (a) an indolocarbazole;
   (b) between about 1% and about 99% by weight inclusive of a selected organic solvent;
   (c) between about 0.25% and about 10% by weight inclusive of a dispersant;
   (d) between about 1% and about 97% by weight inclusive of water; and
   (e) between about 1% and about 60% by weight inclusive of polyethylene glycol.

2. The solution of claim 1 wherein the concentration of said indolocarbazole is at least about 100 μg/ml.

3. The solution of claim 1 wherein the selected organic solvent is selected from the group consisting of propylene glycol, polyethylene glycol, benzyl alcohol, N-N-dimethyl acetamide, ethyl acetate and acetic acid.

4. The solution of claim 1 wherein said selected organic solvent in propylene glycol.

5. The solution of claim 1 wherein said dispersant is selected from the group consisting of polyvinylpyrrolidone, dextran, cellulose, polyoxyethylene sorbitan fatty acid ester, polyethylene glycol 4-isooctylphenyl ether and non-cytotoxic detergent.

6. The solution of claim 1 wherein said dispersant is polyvinylpyrrolidone.

7. The solution of claim 1 comprising between about 30% and about 97% by weight inclusive of water.

8. The solution of claim 7 comprising between about 50% and about 97% by weight inclusive of water.

9. The solution of claim 1 comprising between about 1% and about 40% by weight inclusive of polyethylene glycol.

10. The solution of claim 9 comprising between about 1% and about 30% by weight inclusive of polyethylene glycol.

11. A solution comprising:
   (a) an indolocarbazole
   (b) between about 1% and about 99% by weight inclusive of a selected organic solvent; and
   (c) between about 0.25% and about 10% by weight inclusive of a dispersant.

12. The solution of claim 11 comprising between about 90% and about 99% weight inclusive of a selected organic solvent.

13. The solution of claim 12 comprising between about 1% and about 10% weight inclusive of a dispersant.

14. The solution of claim 11 wherein the selected organic solvent is selected from the group consisting of propylene glycol, polyethylene glycol, benzyl alcohol, N-N-dimethyl acetamide, ethyl acetate and acetic acid.

15. The solution of claim 11 wherein the dispersant is selected from the group consisting of polyvinylpyrrolidone, dextran, cellulose, polyoxyethylene sorbitan fatty acid ester, polyethylene glycol 4-isooctylphenyl ether and non-cytotoxic detergent.

16. A solution comprising:
   (a) about 1% by weight inclusive of the selected organic solvent propylene glycol;
   (b) about 1% by weight inclusive of the dispersant polyvinylpyrrolidone having a k value of 17;
   (c) about 1% by weight inclusive of polyethylene glycol; and
   (d) about 97% by weight inclusive of water.

17. The solution of claim 16 where the concentration of the indolocarbazole is between about 100 μg/ml and about 1 mg/ml.

18. The solution of claim 16 wherein the polyethylene glycol has an average molecular weight of between about 200 and about 400.

19. An aqueous solution comprising:
   a) at least about 0.5 mg/ml of an indolocarbazole;
   b) between about 30% and 60% by weight inclusive of a polyethylene glycol; and
   c) at least one of
      i) between about 1% and about 15% by weight inclusive of a polyoxyethylene sorbitan fatty acid ester;
      ii) between about 1% and about 5% by weight inclusive of benzyl alcohol;
      iii) between about 5% and about 15% by weight inclusive of a polyethylene glycol 4-isooctylphenyl ether; or
      iv) between about 1% and about 5% by weight inclusive of a non-cytotoxic detergent.

20. An aqueous solution comprising:
   a) at least about 0.5 mg/ml of an indolocarbazole;

b) between about 30% and about 60% by weight inclusive of a polyethylene glycol;

c) between about 1% and about 15% by weight inclusive of a polyvinylpyrrolidone; and d) at least one of
   i) between about 1% and about 15% by weight inclusive of a polyoxyethylene sorbitan fatty acid ester;
   ii) between about 1% and about 5% by weight inclusive of benzyl alcohol;
   iii) between about 5% and about 15% by weight inclusive of a polyethylene glycol 4-isooctylphenyl ether; or
   iv) between about 1% and about 5% by weight inclusive of a non-cytotoxic detergent.

21. An aqueous solution comprising:

a) at least about 0.5 mg/ml of an indolocarbazole;

b) between about 30% and about 60% by weight inclusive of a polyethylene glycol;

c) between about 1% and about 15% by weight inclusive of a polyvinylpyrrolidone; and d) between about 1% and about 5% by weight inclusive of benzyl alcohol.

22. The aqueous solution of claim 21, said aqueous solution further comprising at least one of between about 1% and about 15% by weight inclusive of a polyoxyethylene sorbitan fatty acid ester, between about 5% and about 15% by weight inclusive of a polyethylene glycol 4-isooctylphenyl ether or between about 1% and about 5% by weight inclusive of a non-cytotoxic detergent.

23. A solution comprising:

(a) an indolocarbazole;

(b) between about 50% and about 99% by weight inclusive of the selected organic solvent propylene glycol; and (c) between about 0.25% and about 10% by weight inclusive of the dispersant polyvinylpyrrolidone having a k value of 17.

24. The solution of claim 23 wherein the concentration of the indolocarbazole is at least about 5 mg/ml.

* * * * *